United States Patent
Adachi

(10) Patent No.: US 10,441,149 B2
(45) Date of Patent: Oct. 15, 2019

(54) IMAGING DEVICE, ENDOSCOPE, AND ENDOSCOPE SYSTEM

(71) Applicant: OLYMPUS CORPORATION, Tokyo (JP)

(72) Inventor: Satoru Adachi, Tsuchiura (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/940,008

(22) Filed: Mar. 29, 2018

(65) Prior Publication Data

US 2018/0220881 A1    Aug. 9, 2018

Related U.S. Application Data

(63) Continuation of application No. PCT/JP2016/074413, filed on Aug. 22, 2016.

(30) Foreign Application Priority Data

Sep. 30, 2015   (JP) .................................. 2015-193983

(51) Int. Cl.
*A61B 1/06* (2006.01)
*H04N 7/18* (2006.01)
(Continued)

(52) U.S. Cl.
CPC ........ *A61B 1/0638* (2013.01); *A61B 1/00006* (2013.01); *A61B 1/00009* (2013.01);
(Continued)

(58) Field of Classification Search
CPC .................................................. A61B 1/0638
See application file for complete search history.

(56) References Cited

U.S. PATENT DOCUMENTS 10,128,415 B2 * 11/2018 Huang .................... H01L 33/50
2008/0198112 A1 * 8/2008 Roberts ................ G09G 3/3413
345/88

(Continued)

FOREIGN PATENT DOCUMENTS

JP       H06261326 A     9/1994
JP       2006341078 A   12/2006
(Continued)

OTHER PUBLICATIONS

International Search Report dated Oct. 25, 2016 issued in PCT/JP2016/074413.

(Continued)

*Primary Examiner* — James M Pontius
(74) *Attorney, Agent, or Firm* — Scully, Scott, Murphy & Presser, P.C.

(57) ABSTRACT

An imaging device includes: plural pixels; a color filter including a blue filter having spectral characteristics where a maximum value of its transmission spectrum is in the blue wavelength band and transmittance of the wavelength band of a narrow band light is higher than the transmission spectrum in the red and green wavelength bands, a red and green filters having spectral characteristics where minimum values of their transmission spectra are near the maximum value of the transmission spectrum of the blue wavelength band, and having spectral characteristics where their transmission spectra gradually increase toward a short wavelength side from 440 nm; and a control unit configured to execute control of making an accumulation time of a pixel of the plural pixels shorter than accumulation times of pixels having other filters arranged thereon, the pixel having highest spectral sensitivity to the narrow band light.

13 Claims, 15 Drawing Sheets

(51) Int. Cl.

| | | |
|---|---|---|
| *A61B 1/045* | (2006.01) | |
| *A61B 1/05* | (2006.01) | |
| *H04N 5/353* | (2011.01) | |
| *H04N 9/04* | (2006.01) | |
| *H04N 9/07* | (2006.01) | |
| *H04N 5/232* | (2006.01) | |
| *H04N 5/355* | (2011.01) | |
| *H04N 5/357* | (2011.01) | |
| *A61B 1/00* | (2006.01) | |
| *A61B 1/07* | (2006.01) | |
| *H04N 5/225* | (2006.01) | |

(52) U.S. Cl.
CPC .......... *A61B 1/00186* (2013.01); *A61B 1/045* (2013.01); *A61B 1/051* (2013.01); *A61B 1/0646* (2013.01); *A61B 1/07* (2013.01); *H04N 5/232* (2013.01); *H04N 5/353* (2013.01); *H04N 5/3575* (2013.01); *H04N 5/35554* (2013.01); *H04N 7/18* (2013.01); *H04N 9/045* (2013.01); *H04N 9/07* (2013.01); *H04N 7/183* (2013.01); *H04N 2005/2255* (2013.01)

(56) References Cited

U.S. PATENT DOCUMENTS

| | | |
|---|---|---|
| 2009/0023991 A1 | 1/2009 | Gono et al. |
| 2010/0188543 A1 | 7/2010 | Oike |
| 2013/0002917 A1 | 1/2013 | Oike |
| 2013/0194471 A1 | 8/2013 | Yamashita |
| 2014/0055982 A1* | 2/2014 | Tao ............ F21V 33/0052 362/84 |
| 2014/0267657 A1 | 9/2014 | Takei et al. |
| 2014/0362264 A1 | 12/2014 | Oike |
| 2015/0109499 A1 | 4/2015 | Yamashita |
| 2015/0358568 A1 | 12/2015 | Oike |
| 2016/0202555 A1* | 7/2016 | Tanaka ............ G02B 5/201 349/71 |
| 2016/0270642 A1 | 9/2016 | Morita |
| 2016/0353040 A1 | 12/2016 | Yamashita |
| 2017/0231502 A1 | 8/2017 | Nagaoka |

FOREIGN PATENT DOCUMENTS

| | | |
|---|---|---|
| JP | 2010177321 A | 8/2010 |
| JP | 2012170639 A | 9/2012 |
| JP | 2013157883 A | 8/2013 |
| WO | 2013164962 A1 | 11/2013 |
| WO | 2015093295 A1 | 6/2015 |
| WO | 2016080130 A1 | 5/2016 |

OTHER PUBLICATIONS

Japanese Office Action dated Dec. 26, 2017 issued in JP 2017-543013.

* cited by examiner

FIG.17

|  | R-FILTER | G-FILTER | B-FILTER |
|---|---|---|---|
| SPECIAL LIGHT SOURCE | 1 | 1 | 3 |
| WHITE LIGHT SOURCE | 3 | 2 | 3 |

FIG.18

|  | R-FILTER | G-FILTER | B-FILTER |
|---|---|---|---|
| SPECIAL LIGHT SOURCE | 3 | 3 | 1 |
| WHITE LIGHT SOURCE | 2 | 3 | 2 |

IMAGING DEVICE, ENDOSCOPE, AND ENDOSCOPE SYSTEM

CROSS-REFERENCE TO RELATED APPLICATION

This application is a continuation of PCT International Application No. PCT/JP2016/074413 filed on Aug. 22, 2016 which claims the benefit of priority from Japanese Patent Application No. 2015-193983, filed on Sep. 30, 2015, the entire contents of which are incorporated herein by reference.

BACKGROUND

The present disclosure relates to an imaging device, an endoscope, and an endoscope system.

In recent years, for endoscope systems, a technique for highlighting capillary vessels and mucosal microscopic patterns of a mucous membrane by: irradiation of an observed region of a subject with light of narrow bands (hereinafter, referred to as "narrow band light") that are narrower than wavelength bands of light emitted by a white light source and that are respectively included in blue and green wavelength bands; and imaging of reflected light reflected from this observed region, has been known (see Japanese Patent Application Laid-open No. 2012-170639). According to this technique, in an imaging element having a color filter provided on a light receiving surface thereof, the color filter having three types of filters arranged in a predetermined pattern, the three types of filters respectively transmitting red (R), green (G), and blue (B), the filters (G-filters) that transmit green components are characterized in that the G-filters are each provided with, in addition to a primary sensitive region sensitive to green light, a secondary sensitive region sensitive to blue narrow band light.

According to the technique described in Japanese Patent Application Laid-open No. 2012-170639, by execution of correlation operations on pixel values of pixels (G-pixels) that receive light that has been transmitted through the G-filters and pixel values of pixels (R-pixels) that receive light that has been transmitted through the filters (R-filters) transmitting red components, pixel values in the secondary sensitive region are extracted from the pixel values of the G-pixels; and based on the extracted pixel values in the secondary sensitive region and pixel values of pixels (B-pixels) that receive light that has been transmitted through the filters (B-filters) transmitting components in the secondary sensitive region and blue components, a highlighted image, in which capillary vessels, mucosal microscopic patterns, and the like of a mucous membrane have been highlighted, is displayed on a display monitor.

SUMMARY

According to one aspect of the present disclosure, there is provided an imaging device for capturing an image of a subject irradiated with white light including a red wavelength band, a green wavelength band, and a blue wavelength band, or with narrow band light of a narrow band narrower than a wavelength band of the white light, and generating image data, the imaging device including: plural pixels arranged in a two-dimensional matrix, and configured to receive light from outside, generate imaging signals according to amounts of the received light, and output the imaging signal via one of vertical lines, the plural pixels having a horizontal two-shared pixel configuration for outputting the imaging signal by sharing one vertical line between horizontally neighboring two pixels; a color filter including a blue filter having spectral characteristics where a maximum value of its transmission spectrum is in the blue wavelength band and transmittance of the wavelength band of a narrow band light is higher than the transmission spectrum in the red and green wavelength bands, a red filter having spectral characteristics where a maximum value of its transmission spectrum is in the red wavelength band and a minimum value of its transmission spectrum is near the maximum value of the transmission spectrum of the blue wavelength band, and having spectral characteristics where its transmission spectrum gradually increases toward a short wavelength side from 440 nm, and a green filter having spectral characteristics where a maximum value of its transmission spectrum is in the green wavelength band and a minimum value of its transmission spectrum is near the maximum value of the transmission spectrum of the blue wavelength band, and having spectral characteristics where its transmission spectrum gradually increases toward a short wavelength side from 440 nm, wherein the blue filter, the red filter, and the green filter are respectively arranged correspondingly to the plural pixels; and a control unit configured to execute control of making an accumulation time of a pixel of the plural pixels shorter than accumulation times of pixels having other filters arranged thereon, the pixel having highest spectral sensitivity to the narrow band light.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 17 is a diagram schematically illustrating a sensitivity ratio of each filter for each light source;

FIG. 18 is a diagram schematically illustrating an example of accumulation time information recorded in an accumulation time memory according to the third embodiment.

DETAILED DESCRIPTION

Hereinafter, as modes for implementation (hereinafter, referred to as "embodiments"), endoscope systems, each of which includes an endoscope having a distal end to be inserted in a subject, will be described. Further, the present disclosure is not limited by these embodiments. Furthermore, description will be made with the same portions being assigned with the same reference signs, throughout the drawings. Moreover, the drawings are schematic, and it needs to be noted that a relation between a thickness and a width of each member and ratios among respective members may be different from the actual relation and ratios. In addition, there may be portions that differ in their dimensions and ratios among the drawings, too.

Configuration of Endoscope System

Figure 1:
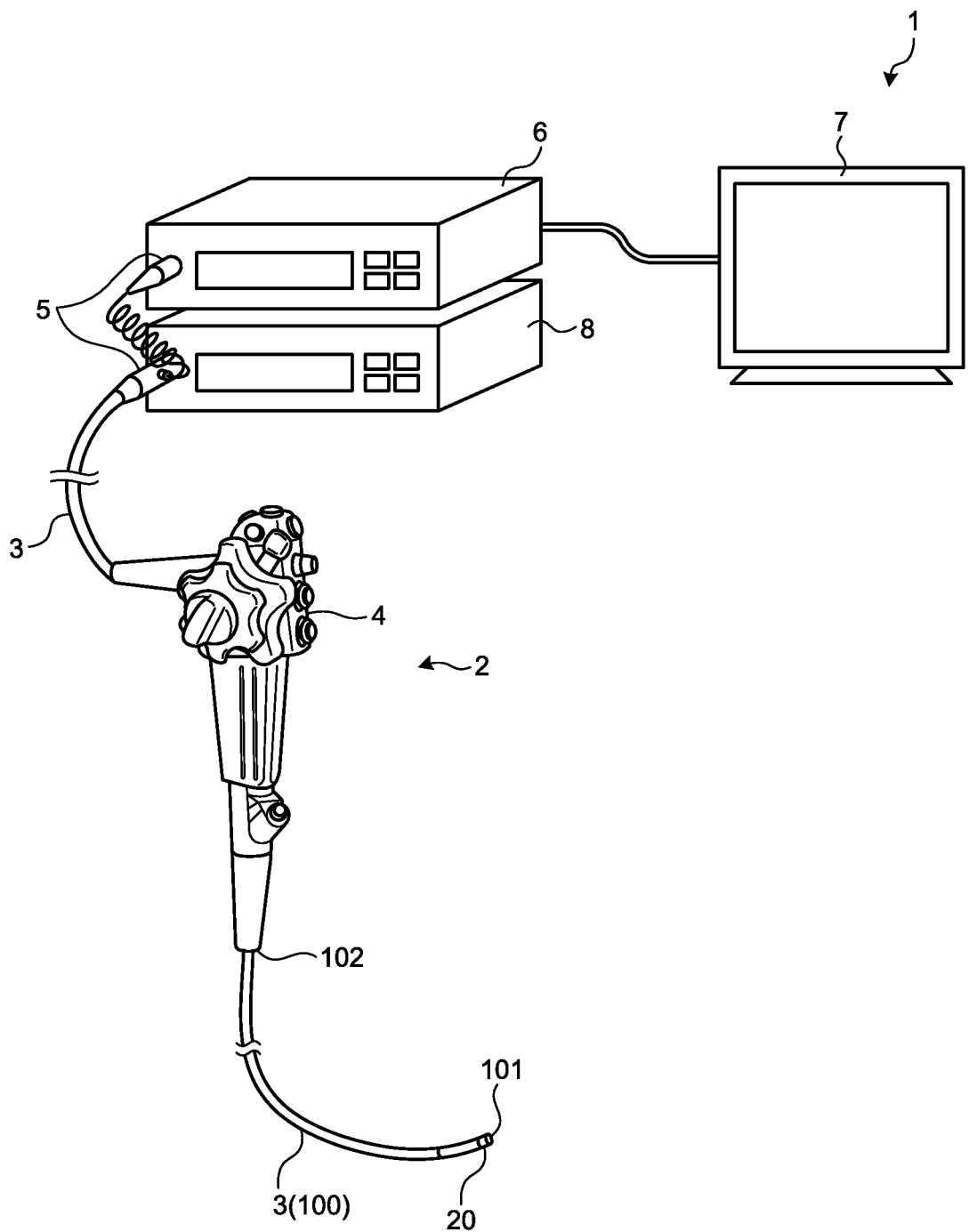
FIG. 1 is a schematic diagram schematically illustrating an overall configuration of an endoscope system according to a first embodiment.

FIG. 1 is a schematic diagram schematically illustrating an overall configuration of an endoscope system according to a first embodiment. An endoscope system 1 illustrated in FIG. 1 includes an endoscope 2, a transmission cable 3, a connector unit 5, a processor 6 (processing device), a display device 7, and a light source device 8.

By insertion of an insertion portion 100, which is a part of the transmission cable 3, into a body cavity of a subject; the endoscope 2 captures in-vivo images of the subject and outputs imaging signals (image data) to the processor 6. Further, in the endoscope 2: an imaging unit 20 (imaging device), which captures the in-vivo images, is provided at a distal end 101 of the insertion portion 100 to be inserted in a body cavity of the subject, the distal end 101 being at one end of the transmission cable 3; and an operating unit 4, which receives various operations for the endoscope 2, is provided at a proximal end 102 of the insertion portion 100. The imaging signals of the images captured by the imaging unit 20, for example, pass through the transmission cable 3 having a length of a few meters, and are output to the connector unit 5.

The transmission cable 3 connects between the endoscope 2 and the connector unit 5, and connects between the endoscope 2 and the light source device 8. Further, the transmission cable 3 propagates therethrough the imaging signals generated by the imaging unit 20, to the connector unit 5. The transmission cable 3 is configured by use of a cable, an optical fiber, or the like.

The connector unit 5: is connected to the endoscope 2, the processor 6, and the light source device 8; performs predetermined signal processing on the imaging signals output by the endoscope 2 connected thereto; converts (A/D-converts) the imaging signals that are analog, to digital imaging signals; and outputs the converted imaging signals to the processor 6.

The processor 6 executes predetermined image processing on the imaging signals input from the connector unit 5, and outputs the image processed imaging signals to the display device 7. Further, the processor 6 integrally controls the overall endoscope system 1. For example, the processor 6 executes control of switching among illumination light beams emitted by the light source device 8 and switching among imaging modes of the endoscope 2.

The display device 7 displays images corresponding to the imaging signals that have been image-processed by the processor 6. Further, the display device 7 displays thereon various types of information related to the endoscope system 1. The display device 7 is configured by use of a liquid crystal or electro-luminescence display panel or the like.

The light source device 8 emits illumination light to the subject from the distal end 101 of the insertion portion 100 of the endoscope 2 via the connector unit 5 and the transmission cable 3. The light source device 8 is configured by use of: a white light emitting diode (LED) that emits white light; an LED that emits special light of narrow band light having a wavelength band narrower than a wavelength band of the white light; and the like. The light source device 8 emits, under the control by the processor 6, the white light or the narrow band light, to the subject, via the endoscope 2. In this first embodiment, for the light source device 8, a simultaneous illumination method is adopted.

Figure 2:
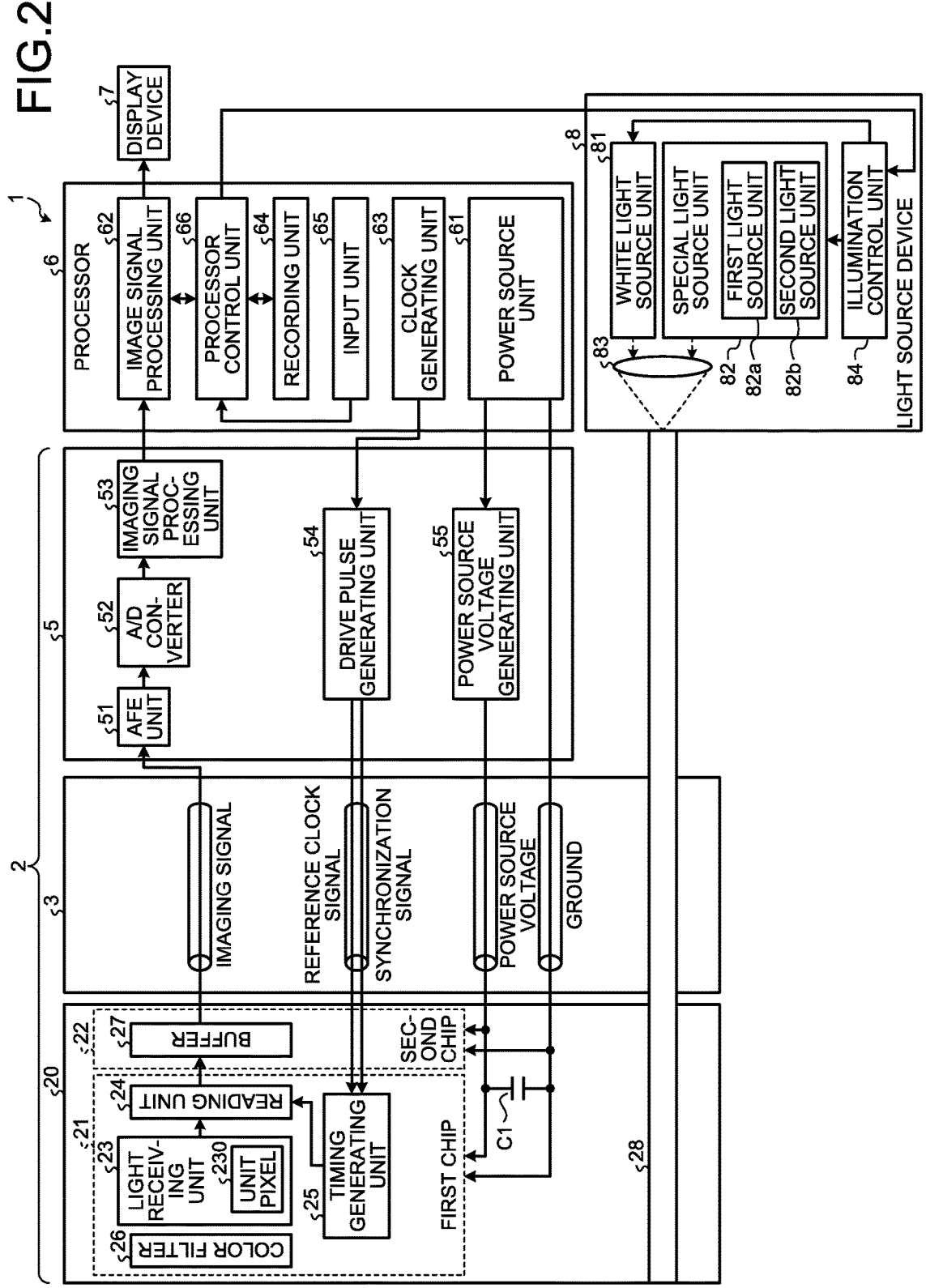
FIG. 2 is a block diagram illustrating functions of main parts of the endoscope system according to the first embodiment.

FIG. 2 is a block diagram illustrating functions of main parts of the endoscope system 1. By reference to FIG. 2, details of a configuration of each unit of the endoscope system 1 and paths of electric signals in the endoscope system 1 will be described.

Configuration of Endoscope

Firstly, a configuration of the endoscope 2 will be described. The endoscope 2 illustrated in FIG. 2 includes the imaging unit 20, the transmission cable 3, and the connector unit 5.

The imaging unit 20 has a first chip 21 (imaging element) and a second chip 22. Further, the imaging unit 20 receives, via the transmission cable 3, power source voltage VDD generated by a later described power source voltage generating unit 55 of the connector unit 5, together with ground GND. Between the power source voltage VDD and the ground GND that are supplied to the imaging unit 20, a condenser C1 for power source stabilization is provided.

The first chip 21 has: a light receiving unit 23 having plural unit pixels 230 arranged therein, which are arranged in a two-dimensional matrix, receive light from outside, and generate and output image signals according to amounts of the light received; a reading unit 24 that reads imaging signals photoelectrically converted respectively by the plural unit pixels 230 in the light receiving unit 23; a timing generating unit 25 that generates, based on a reference clock signal and a synchronization signal that are input from the connector unit 5, a timing signal, and outputs the timing signal to the reading unit 24; and a color filter 26 that is arranged on a light receiving surface of each of the plural unit pixels 230. A detailed configuration of the first chip 21 will be described later.

Figure 3:
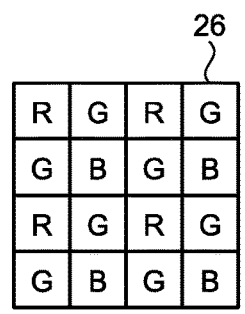
FIG. 3 is a diagram schematically illustrating a configuration of a color filter according to the first embodiment.

FIG. 3 is a diagram schematically illustrating a configuration of the color filter 26. As illustrated in FIG. 3, the color filter 26 is realized by use of color filters in a Bayer array formed of: red filters (hereinafter, referred to as "R-filters"), each of which has spectral characteristics where a maximum value of its transmission spectrum is in a red wavelength band, and transmittance of a wavelength band of the narrow band light is higher than the transmission spectrum in green and blue wavelength bands; green filters (hereinafter, referred to as "G-filters"), each of which has spectral characteristics where a maximum value of its transmission spectrum is in the green wavelength band, and transmittance of the wavelength band of the narrow band light is higher than the transmission spectrum in the red and blue wavelength bands; and blue filters (hereinafter, referred to as "B-filters"), each of which has spectral characteristics where a maximum value of its transmission spectrum is in the blue wavelength band, and transmittance of the wavelength band of the narrow band light is higher than the transmission spectrum in the red and green wavelength bands. In the color filter 26, the R-filters, G-filters, B-filters, and G-filters are respectively arranged on the unit pixels 230. Specifically, in the color filter 26, the G-filters and B-filters are alternately arranged on even-numbered lines of the light receiving unit 23 in this order, and R-filters and G-filters are alternately arranged on odd-numbered lines of the light receiving unit 23 in this order. Further, hereinafter, the unit pixels 230 having the R-filters arranged on their light receiving surfaces will be referred to as R-pixels, the unit pixels 230 having the G-filters arranged thereon as G-pixels, and the unit pixels 230 having the B-filters arranged thereon as B-pixels.

Figure 4:
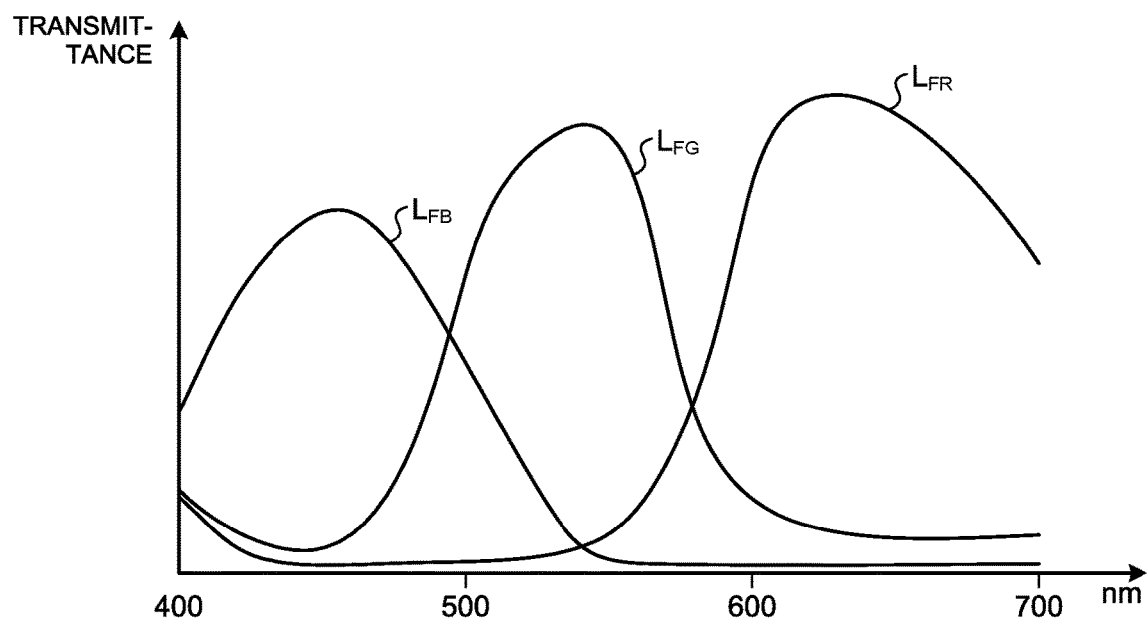
FIG. 4 is a diagram illustrating spectral sensitivity characteristics of each filter illustrated in FIG. 3.

FIG. 4 is a diagram illustrating spectral transmittance characteristics of each filter illustrated in FIG. 3. In FIG. 4, the horizontal axis represents wavelength (nm), and the vertical axis represents transmittance. Further, in FIG. 4, a curve $L_{FB}$ represents transmittance characteristics of the B-filters, a curve $L_{FG}$ represents transmittance characteristics of the G-pixels, and a curve $L_{FR}$ represents transmittance characteristics of the R-pixels.

As represented by the curve $L_{FR}$ in FIG. 4, the R-filters have spectral characteristics where a maximum value of their transmission spectrum is in the red wavelength band, and transmittance of a wavelength band of narrow band light described later is higher than the transmission spectrum in the green and blue wavelength bands. Specifically, the R-filters have spectral characteristics where a minimum value of their transmission spectrum is near a maximum value of a transmission spectrum of the B-filters, and their transmittance gradually increases toward a short wavelength side. More specifically, the R-filters have spectral characteristics where their transmittance gradually increases toward the short wavelength side, from 440 nm. Further, as represented by the curve $L_{FG}$ in FIG. 4, the G-filters have spectral characteristics where a maximum value of their transmission spectrum is in the green wavelength band, and transmittance of the wavelength band of the narrow band light described later is higher than the transmission spectrum in the red and blue wavelength bands. Specifically, the G-filters have spectral characteristics where a minimum value of their transmission spectrum is near the maximum value of the transmission spectrum of the B-filters, and their transmittance gradually increases toward the short wavelength side. More specifically, the G-filters have spectral characteristics where their transmittance gradually increases toward the short wavelength side from 440 nm. Furthermore, as represented by the curve $L_{FB}$ in FIG. 4, the B-filters have spectral characteristics where the maximum value of their transmission spectrum is in the blue wavelength band, and transmittance of the wavelength band of the narrow band light described later is higher than the transmission spectrum in the red and green wavelength bands. Specifically, the B-filters have spectral characteristics where their transmittance gradually decreases toward the short wavelength side from around the maximum value of their transmission spectrum.

By reference back to FIG. 2, a configuration of each unit of the endoscope system 1 will be described.

The second chip 22 has a buffer 27 that amplifies an imaging signal output from each of the plural unit pixels 230 in the first chip 21, and outputs the amplified imaging signal to the transmission cable 3. Combinations of circuits arranged on the first chip 21 and the second chip 22 may be modified as appropriate. For example, the timing generating unit 25 arranged on the first chip 21 may be arranged on the second chip 22 instead.

Illumination light emitted from the light source device 8 is emitted toward the subject through a light guide 28. The light guide 28 is realized by use of a glass fiber, an illumination lens, or the like.

The connector unit 5 has an analog front end unit 51 (hereinafter, referred to as "AFE unit 51"), an A/D converter 52, an imaging signal processing unit 53, a drive pulse generating unit 54, and a power source voltage generating unit 55.

The AFE unit 51 receives an imaging signal propagated from the imaging unit 20; and after performing impedance matching by using a passive element, such as a resistance, takes out an alternating current component by using a condenser, and determines an operating point by using a partial resistance. Thereafter, the AFE unit 51 corrects the imaging signal (analog signal), and outputs the corrected imaging signal to the A/D converter 52.

The A/D converter 52 converts the analog imaging signal input from the AFE unit 51 to a digital imaging signal, and outputs the digital imaging signal to the imaging signal processing unit 53.

The imaging signal processing unit 53 is formed of, for example, a field programmable gate array (FPGA), performs processing, such as noise removal and format conversion processing, on the digital imaging signal input from the A/D converter 52, and outputs the processed imaging signal to the processor 6.

The drive pulse generating unit 54 generates, based on a reference clock signal (for example, a clock signal of 27 MHz), which is supplied from the processor 6 and serves as a reference for operation of each unit forming the endoscope 2, a synchronization signal indicating a start position of each frame, and outputs, together with the reference clock signal, the generated synchronization signal, to the timing generating unit 25 of the imaging unit 20, via the transmission cable 3. The synchronization signal generated by the drive pulse generating unit 54 includes a horizontal synchronization signal and a vertical synchronization signal.

The power source voltage generating unit 55 generates, from power supplied from the processor 6, a power source voltage needed to drive the first chip 21 and the second chip 22, and outputs the power source voltage to the first chip 21 and the second chip 22. The power source voltage generating unit 55 generates the power source voltage needed to drive the first chip 21 and the second chip 22, by using a regulator or the like.

Configuration of Processor

Next, a configuration of the processor 6 will be described.

The processor 6 is a control device that integrally controls the overall endoscope system 1. The processor 6 includes a power source unit 61, an image signal processing unit 62, a clock generating unit 63, a recording unit 64, an input unit 65, and a processor control unit 66.

The power source unit 61 generates the power source voltage VDD, and supplies this power source voltage VDD generated, together with the ground (GND), to the power source voltage generating unit 55 of the connector unit 5.

The image signal processing unit 62 converts the digital imaging signal that has been signal-processed by the imaging signal processing unit 53, to an image signal by executing image processing, such as synchronization processing, white balance (WB) adjustment processing, gain adjustment processing, gamma correction processing, digital/analog (D/A) conversion processing, and format conversion processing, on the digital imaging signal, and outputs this image signal to the display device 7.

The clock generating unit 63 generates the reference clock signal serving as reference for operation of each unit forming the endoscope system 1, and outputs this reference clock signal to the drive pulse generating unit 54.

The recording unit 64 records therein various types of information related to the endoscope system 1, data being processed, and the like. The recording unit 64 is configured by use of a recording medium, such as a flash memory or a random access memory (RAM).

The input unit 65 receives input of various operations related to the endoscope system 1. For example, the input unit 65 receives input of an instruction signal for switching among types of illumination light emitted by the light source device 8. The input unit 65 is configured by use of, for example, a cross switch, push buttons, and the like.

The processor control unit 66 integrally controls the respective units forming the endoscope system 1. The processor control unit 66 is configured by use of a central processing unit (CPU) or the like. The processor control unit 66 performs switching among illumination light beams emitted by the light source device 8, according to an instruction signal input from the input unit 65.

Configuration of Light Source Device

Next, a configuration of the light source device 8 will be described. The light source device 8 includes a white light source unit 81, a special light source unit 82, a condenser lens 83, and an illumination control unit 84.

Under control by the illumination control unit 84, the white light source unit 81 emits white light toward the light guide 28 via the condenser lens 83. The white light source unit 81 is configured by use of a white light emitting diode (LED). In this first embodiment, the white light source unit 81 is formed of a white LED, but, for example, a Xenon lamp, or a combination of a red LED, a green LED, and a blue LED may be caused to emit white light.

Under control by the illumination control unit 84, the special light source unit 82 simultaneously emits two narrow band light beams of wavelength bands different from each other, toward the light guide 28 via the condenser lens 83. The special light source unit 82 has a first light source unit 82a, and a second light source unit 82b.

The first light source unit 82a is configured by use of a purple LED. Under control by the illumination control unit 84, the first light source unit 82a emits narrow band light of a narrow band narrower than the blue wavelength band. Specifically, under control by the illumination control unit 84, the first light source unit 82a emits narrow band light of a wavelength band of 390 nm to 440 nm.

The second light source unit 82b is configured by use of a green LED. Under control by the illumination control unit 84, the second light source unit 82b emits narrow band light of a narrow band narrower than the green wavelength band. Specifically, under control by the illumination control unit 84, the second light source unit 82b emits narrow band light of a wavelength band of 530 nm to 550 nm.

Figure 5:
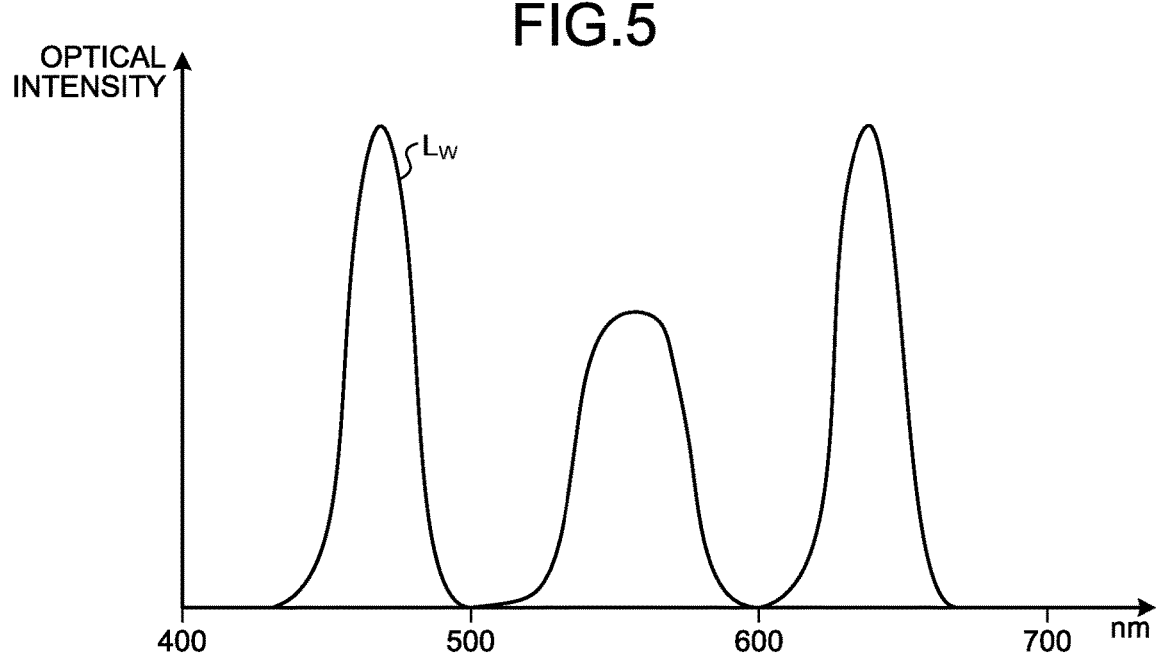
FIG. 5 is a diagram schematically illustrating spectral characteristics of white light emitted by a white light source unit of a light source device according to the first embodiment.
Figure 6:
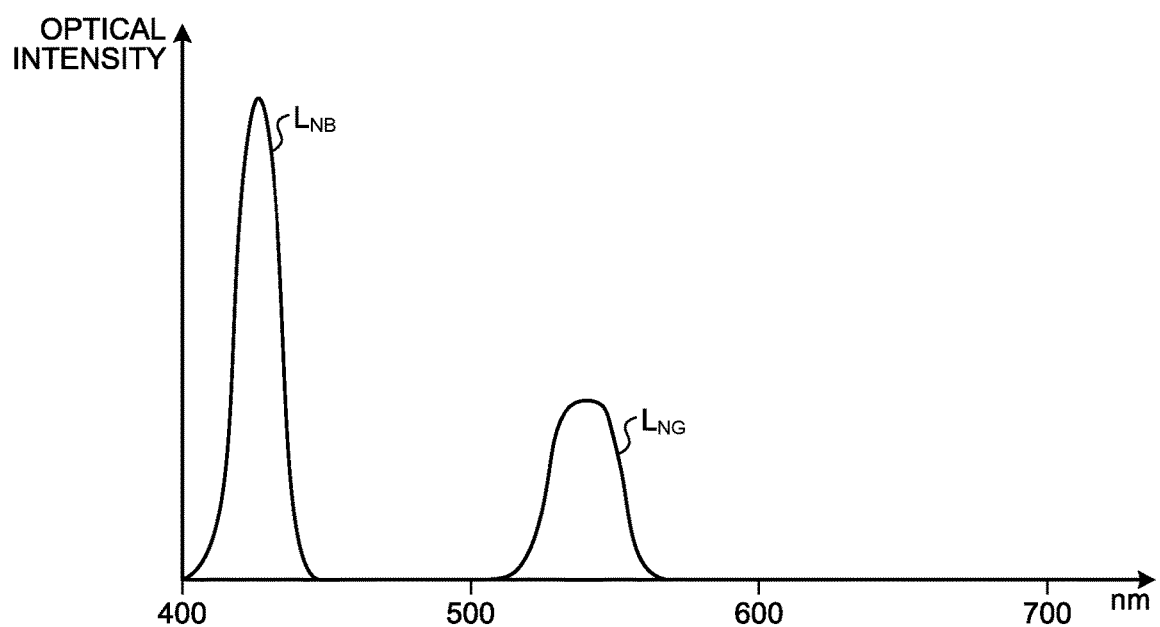
FIG. 6 is a diagram schematically illustrating spectral characteristics of two mutually different narrow band light beams emitted by a special light source unit of the light source device according to the first embodiment.

FIG. 5 is a diagram schematically illustrating spectral characteristics of the white light emitted by the white light source unit 81. FIG. 6 is a diagram schematically illustrating spectral characteristics of the two narrow band light beams emitted by the special light source unit 82, the two narrow band light beams having wavelength bands different from each other. In FIG. 5 and FIG. 6, the horizontal axis represents wavelength (nm) and the vertical axis represents optical intensity. In FIG. 5, a curve $L_W$ represents spectral characteristics of the white light emitted by the white light source unit 81. Further, in FIG. 6, a curve $L_{NB}$ represents spectral characteristics of the narrow band light emitted by the first light source unit 82a, and a curve $L_{NG}$ represents spectral characteristics of the narrow band light emitted by the second light source unit 82b.

As represented by the curve $L_W$ in FIG. 5, the white light source unit 81 emits the white light including each of the red wavelength band, the green wavelength band, and the blue wavelength band. Further, as represented by the curve $L_{NB}$ in FIG. 6, the first light source unit 82a emits the narrow band light of the narrow band (390 nm to 440 nm) narrower than the blue wavelength band. Further, as represented by the curve $L_{NG}$ in FIG. 6, the second light source unit 82b emits the narrow band light of the narrow band (530 nm to 550 nm) narrower than the green wavelength band. Furthermore, as illustrated in FIG. 6, if an NBI observation mode has been set in the endoscope system 1, the illumination control unit 84 executes, based on a sensitivity ratio of each of the plural unit pixels 230, each of which has any one of a red filter, a green filter, and a blue filter arranged thereon, control of causing the first light source unit 82a to emit the narrow band light with intensity of the narrow band light emitted by the first light source unit 82a being made larger than intensity of the narrow band light emitted by the second light source unit 82b. For example, the illumination control unit 84 executes the control, such that the intensity of the narrow band light emitted by the first light source unit 82a becomes approximately five times the intensity of the narrow band light emitted by the second light source unit 82b.

By reference back to FIG. 2, the description of the configuration of the light source device 8 will be continued.

The condenser lens 83 condenses the white light emitted by the white light source unit 81 or the special light emitted by the special light source unit 82, and outputs the condensed light to the light guide 28. The condenser lens 83 is configured by use of one lens or plural lenses.

Under control by the processor control unit 66, the illumination control unit 84 controls the white light source unit 81 and the special light source unit 82. Specifically, under control by the processor control unit 66, the illumination control unit 84 causes the white light source unit 81 to emit the white light or the special light source unit 82 to emit the narrow band light. Further, the illumination control unit 84 controls emission timings, at which the white light source unit 81 emits the white light, or emission timings, at which the special light source unit 82 emits the narrow band light. In this first embodiment, the illumination control unit 84 controls each of the white light source unit 81 and the special light source unit 82, by PWM control. Furthermore, if the NBI observation mode has been set in the endoscope system 1, the illumination control unit 84 causes the first light source unit 82a and the second light source unit 82b to simultaneously emit the two narrow band light beams of wavelength bands different from each other. Moreover, if the NBI observation mode has been set in the endoscope system 1, the illumination control unit 84 executes, based on the sensitivity ratio of each of the plural unit pixels 230 each having any one of a red filter, a green filter, and a blue filter arranged thereon, control of causing the first light source unit 82a to emit the narrow band light with the intensity of the narrow band light emitted by the first light source unit 82a being made larger than the intensity of the narrow band light emitted by the second light source unit 82b.

Detailed Configuration of First Chip

Figure 7:
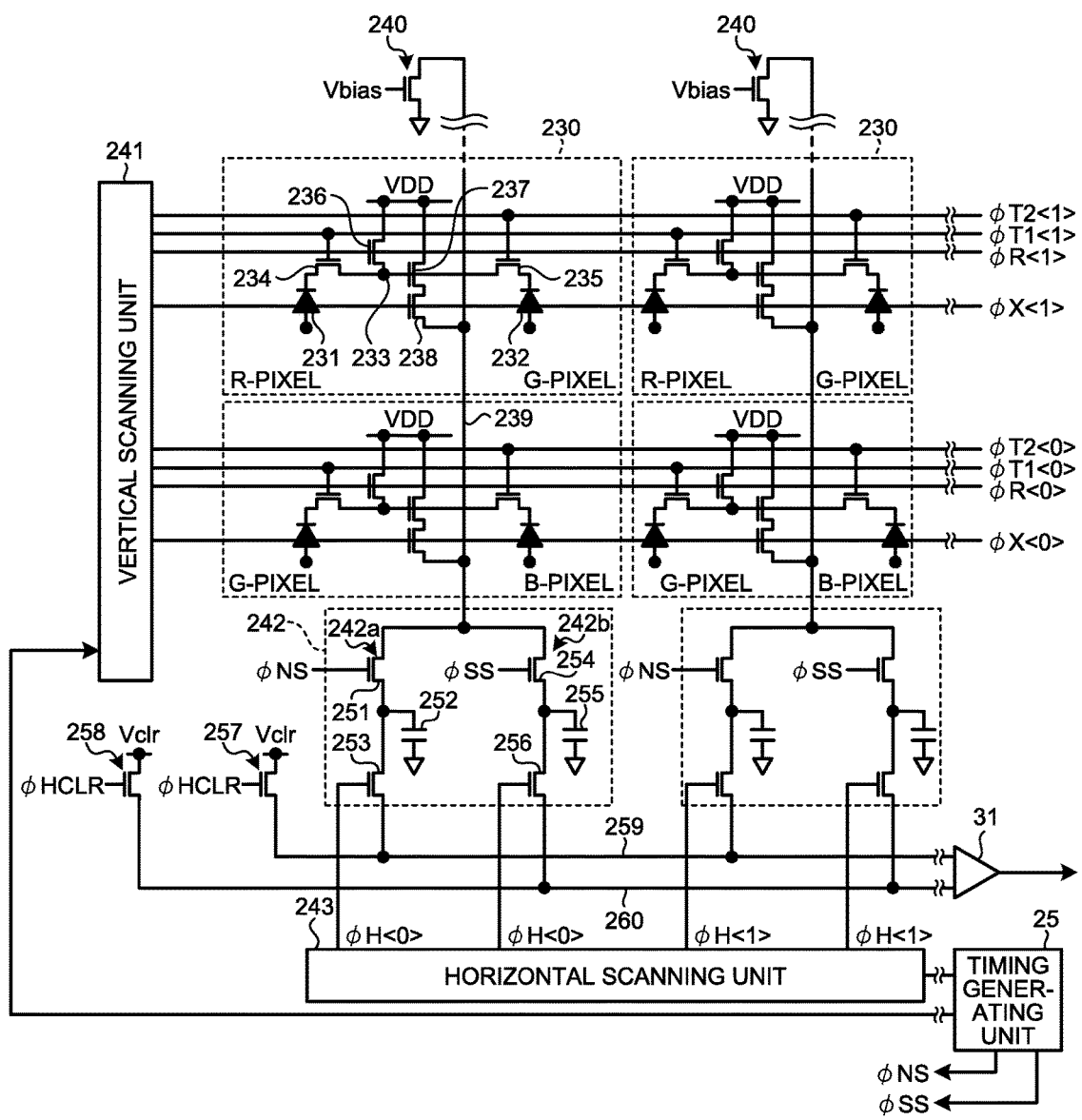
FIG. 7 is a circuit diagram illustrating a detailed configuration of a first chip illustrated in FIG. 2.

Next, a detailed configuration of the first chip 21 mentioned above will be described. FIG. 7 is a circuit diagram illustrating a configuration of the first chip 21.

The first chip 21 illustrated in FIG. 7 includes at least: the timing generating unit 25; an output unit 31 (amplifier); the plural pixels 230; a constant current source 240; a vertical scanning unit 241 (row selecting circuit); a correlated double sampling (CDS) unit 242; a horizontal scanning unit 243 (column selecting circuit); a first horizontal resetting transistor 257; and a second horizontal resetting transistor 258. The vertical scanning unit 241 and the horizontal scanning unit 243 function as the reading unit 24.

Based on the reference clock signal and the synchronization signal, the timing generating unit 25 generates various drive pulses, and outputs the generated drive pulses respectively to the vertical scanning unit 241, the CDS unit 242, and the horizontal scanning unit 243, which will be described later. In this first embodiment, the timing generating unit 25 functions as a control unit that controls an accumulation time, in which each of the plural unit pixels 230 is caused to accumulate optical signal charge.

One end of the constant current source 240 is connected to the ground GND, another end of the constant current source 240 is connected to a vertical transfer line 239, and a signal line, through which a reference voltage Vbias is input, is connected to a gate of the constant current source 240.

The vertical scanning unit 241 causes an imaging signal and a noise signal resulting from pixel resetting, to be transferred to the vertical transfer line 239, and each of the noise signal and the imaging signal to be output to the CDS unit 242, by: applying, based on drive pulses (for example, ΦX, ΦR, ΦT1, and ΦT2) input from the timing generating unit 25, row selection pulses (for example, ΦX<M>, ΦR<M>, ΦT1<M>, and ΦT2<M>) respectively to a selected row <M> (M=0, 1, 2, . . . , m-1, m) of the light receiving unit 23; and driving each of the unit pixels 230 of the light receiving unit 23 with the constant current source 240 connected to the vertical transfer line 239. In this first embodiment, imaging signals are commonly read from two unit pixels 230. Further, in this first embodiment, the vertical transfer line 239 functions as a transfer line.

The CDS unit 242 samples a noise signal resulting from pixel resetting at each unit pixel 230, outputs this sampled noise signal to the output unit 31, samples an imaging signal photoelectrically converted by each unit pixel 230, and outputs this sampled imaging signal to the output unit 31. The CDS unit 242 has a noise sampling unit 242a, and a signal sampling unit 242b.

The noise sampling unit 242a samples a noise signal resulting from pixel resetting at each unit pixel 230, and outputs this sampled noise signal to the output unit 31. The noise sampling unit 242a has a first sampling switch 251, a first sampling unit 252 (capacitor), and a first output switch 253.

One end of the first sampling switch 251 is connected to the vertical transfer line 239, another end of the first sampling switch 251 is connected to one end of the first output switch 253, and a drive pulse ΦNS is input from the timing generating unit 25, to a gate of the first sampling switch 251.

One end of the first sampling unit 252 is connected between the first sampling switch 251 and the first output switch 253, and another end of the first sampling unit 252 is connected to the ground GND. When the drive pulse ΦNS is applied to the gate of the first sampling switch 251 in a case where the row selection pulse ΦX<M> and the drive pulse ΦR<M> have been applied to the unit pixel 230, the first sampling unit 252 samples (holds) the noise signal from the unit pixel 230.

The one end of the first output switch 253 is connected to the first sampling switch 251, another end of the first output switch 253 is connected to a first horizontal transfer line 259, and a drive pulse ΦH<N> is input from the horizontal scanning unit 243, to a gate of the first output switch 253. When the drive pulse ΦH<N> is applied to the gate of the first output switch 253, the first output switch 253 transfers the noise signal sampled by the first sampling unit 252, to the first horizontal transfer line 259.

The signal sampling unit 242b samples the imaging signal photoelectrically converted by each unit pixel 230, and outputs this sampled imaging signal to the output unit 31. The signal sampling unit 242b has a second sampling switch 254, a second sampling unit 255, and a second output switch 256.

One end of the second sampling switch 254 is connected to the vertical transfer line 239, another end of the second sampling switch 254 is connected to one end of the second output switch 256, and a drive pulse ΦSS is input from the timing generating unit 25, to a gate of the second sampling switch 254.

One end of the second sampling unit 255 is connected between the second sampling switch 254 and the second output switch 256, and another end of the second sampling unit 255 is connected to the ground GND. When the drive pulse ΦSS is applied to the gate of the second sampling switch 254 in a case where the row selection pulse ΦX<M>, and the drive pulse ΦT1<M> or the drive pulse ΦT2<M> have been applied to the unit pixel 230, the second sampling unit 255 samples (holds) the imaging signal from the unit pixel 230.

The one end of the second output switch 256 is connected to the second sampling switch 254, another end of the second output switch 256 is connected to a second horizontal transfer line 260, and the drive pulse ΦH<N> is input from the horizontal scanning unit 243, to a gate of the second output switch 256. When the drive pulse ΦH<N> is applied to the gate of the second output switch 256, the second output switch 256 transfers the imaging signal sampled by the second sampling unit 255, to the second horizontal transfer line 260.

The horizontal scanning unit 243 transfers and outputs a noise signal from each unit pixel 230 resulting from pixel resetting at each unit pixel 230, to the first horizontal transfer line 259 via the CDS unit 242, by: applying, based on a drive pulse (ΦH) supplied from the timing generating unit 25, a column selection signal ΦH<N> to a selected column <N> (N=0, 1, 2, 3, . . . , n) of the light receiving unit 23. Further, the horizontal scanning unit 243 transfers and outputs the imaging signal photoelectrically converted by each unit pixel 230, to the second horizontal transfer line 260 via the CDS unit 242, by: applying, based on a drive pulse (ΦH) supplied from the timing generating unit 25, a column selection signal ΦH<N> to a selected column <N> of the light receiving unit 23. In this first embodiment, the vertical scanning unit 241 and the horizontal scanning unit 243 function as the reading unit 24.

In the light receiving unit 23 of the first chip 21, multiple unit pixels 230 are arranged in a two dimensional matrix. Each unit pixel 230 includes: a photoelectric conversion element 231 (photodiode) and a photoelectric conversion element 232; a charge converter 233; a transfer transistor 234 (first transfer unit) and a transfer transistor 235; a charge converter resetting unit 236 (transistor); a pixel source follower transistor 237; and a pixel output switch 238 (signal output unit). In this specification, one or plural photoelectric conversion elements and a transfer transistor for transfer of signal charge from each photoelectric conversion element to the charge converter 233 are called a unit cell. That is, in a unit cell, a set of: one or plural photoelectric conversion elements; and a transfer transistor, is included, and in each unit pixel 230, one unit cell is included. Further, in FIG. 7, the unit pixels 230 respectively having the R-filters, G-filters, and B-filters arranged thereon are written as R-pixels, G-pixels, and B-pixels.

The photoelectric conversion element 231 and the photoelectric conversion element 232 photoelectrically convert incident light to signal electric charge according to the amount of that light. Cathodes of the photoelectric conversion element 231 and photoelectric conversion element 232 are respectively connected to one end of the transfer transistor 234 and one end of the transfer transistor 235, and anodes of the photoelectric conversion element 231 and photoelectric conversion element 232 are connected to the ground GND.

The charge converter 233 is formed of a floating diffusion capacitance (FD), and converts the charge accumulated in the photoelectric conversion element 231 and photoelectric conversion element 232 to voltage.

The transfer transistor 234 and transfer transistor 235 respectively transfer the charge from the photoelectric conversion element 231 and photoelectric conversion element 232, to the charge converter 233. To gates of the transfer transistor 234 and transfer transistor 235, signal lines, through which drive pulses (row selection pulses) ΦT1 and ΦT2 are supplied, are respectively connected, and to the other ends of the transfer transistor 234 and transfer transistor 235, the charge converter 233 is connected. When the drive pulses ΦT1 and ΦT2 are supplied to the transfer transistor 234 and transfer transistor 235 via the signal lines from the vertical scanning unit 241, the transfer transistor 234 and transfer transistor 235 are turned into an ON-state, and transfer the signal charge from the photoelectric conversion element 231 and photoelectric conversion element 232, to the charge converter 233.

The charge converter resetting unit 236 resets the charge converter 233 to a predetermined potential. One end of the charge converter resetting unit 236 is connected to the power source voltage VDD, another end of the charge converter resetting unit 236 is connected to the charge converter 233, and to a gate of the charge converter resetting unit 236, a signal line, through which the drive pulse ΦR is supplied, is connected. When the drive pulse ΦR is supplied to the charge converter resetting unit 236 via the signal line from the vertical scanning unit 241, the charge converter resetting unit 236 is turned into an ON-state, causes the signal charge accumulated in the charge converter 233 to be released, and resets the charge converter 233 to a predetermined potential.

One end of the pixel source follower transistor 237 is connected to the power source voltage VDD, and another end of the pixel source follower transistor 237 is connected to one end of the pixel output switch 238; and a signal voltage-converted by the charge converter 233 (an image signal, or a signal resulting from resetting) is input to a gate of the pixel source follower transistor 237.

The pixel output switch 238 outputs the signal voltage-converted by the charge converter 233, to the vertical transfer line 239. Another end of the pixel output switch 238 is connected to the vertical transfer line 239, and a signal line, through which the drive pulse ΦX is supplied, is connected to a gate of the pixel output switch 238. When the drive pulse ΦX is supplied to the gate of the pixel output switch 238 via the signal line from the vertical scanning unit 241, the pixel output switch 238 is turned into an ON-state, and transfers the imaging signal or the noise signal resulting from resetting, to the vertical transfer line 239.

One end of the first horizontal resetting transistor 257 is connected to the ground GND, another end of the first horizontal resetting transistor 257 is connected to the first horizontal transfer line 259, and a drive pulse ΦHCLR is input from the timing generating unit 25 to a gate of the first horizontal resetting transistor 257. When the drive pulse ΦHCLR is input to the gate of the first horizontal resetting transistor 257 from the timing generating unit 25, the first horizontal resetting transistor 257 is turned into an ON-state, and resets the first horizontal transfer line 259.

One end of the second horizontal resetting transistor 258 is connected to the ground GND, another end of the second horizontal resetting transistor 258 is connected to the second horizontal transfer line 260, and the drive pulse ΦHCLR is input from the timing generating unit 25 to a gate of the second horizontal resetting transistor 258. When the drive pulse ΦHCLR is input to the gate of the second horizontal resetting transistor 258 from the timing generating unit 25, the second horizontal resetting transistor 258 is turned into an ON-state, and resets the second horizontal transfer line 260.

The output unit 31 is configured by use of a differential amplifier, and outputs the imaging signal, from which noise has been removed, by taking a difference between the noise signal transferred from the first horizontal transfer line 259 and the imaging signal transferred from the second horizontal transfer line 260.

Sensitivity of Each Pixel Upon Emission of Narrow Band Light

Figure 8:
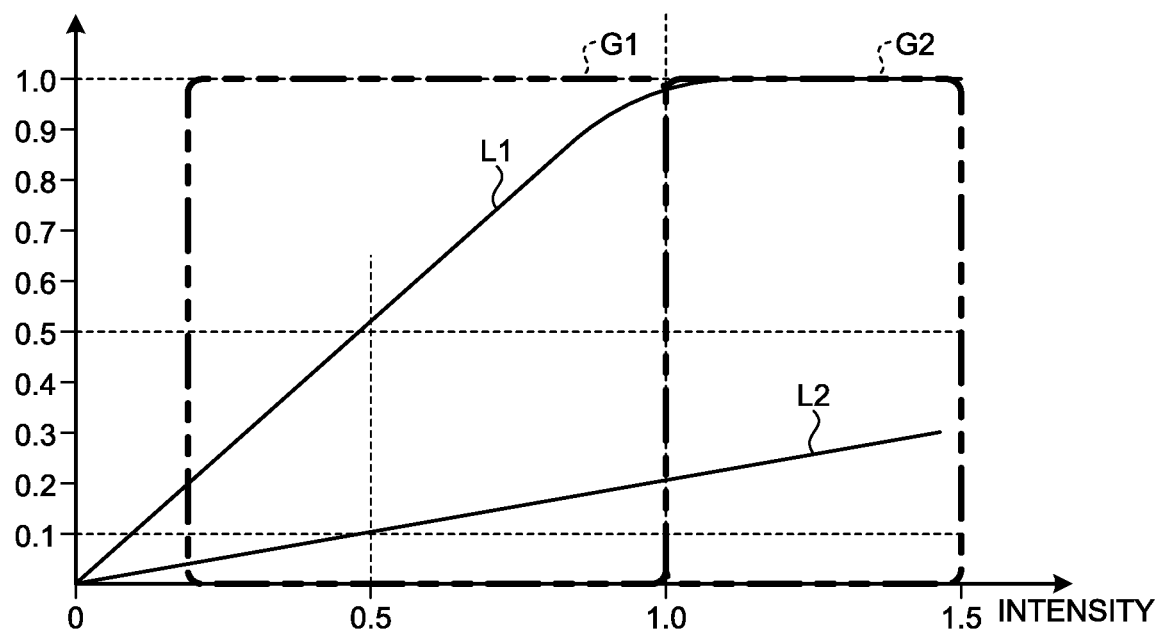
FIG. 8 is a diagram illustrating relations between intensity of narrow band light beam and output value of each pixel when a first light source unit according to the first embodiment emits the narrow band light.

Next, sensitivity of each of the R-pixels, G-pixels, and B-pixels, when the first light source unit 82a emits the narrow band light will be described. FIG. 8 is a diagram illustrating relations between intensity of the narrow band light and output value of each pixel when the first light source unit 82a emits the narrow band light. In FIG. 8, the horizontal axis represents the intensity of the narrow band light emitted by the first light source unit 82a, and the vertical axis represents the output value of each pixel. Further, in FIG. 8, a curve L1 represents the output value (pixel value) of a B-pixel, and a straight line L2 represents the output value (pixel value) of an R-pixel or a G-pixel.

As represented by the straight line L2 in FIG. 8, since sensitivity of each of the R-pixel and the G-pixel to the narrow band (B-light) is low, one may consider increasing the intensity of the narrow band light emitted by the first light source unit 82a. However, as represented by the curve L1 and the straight line L2 in an area G2, when the intensity of the narrow band light emitted by the first light source unit 82a is increased, the output value of the B-pixel is saturated. In contrast, as represented by the curve L1 and the straight line L2 in an area G1, if the first light source unit 81a is caused to emit the narrow band light with its intensity decreased such that the B-pixel is not saturated, an S/N ratio of the output value of each of the R-pixel and G-pixel will be insufficient, and thus this output value will be unable to be used as image information. That is, there has been a problem that for narrow band light in a primary color Bayer array, resolution of an image is degraded.

Figure 9:
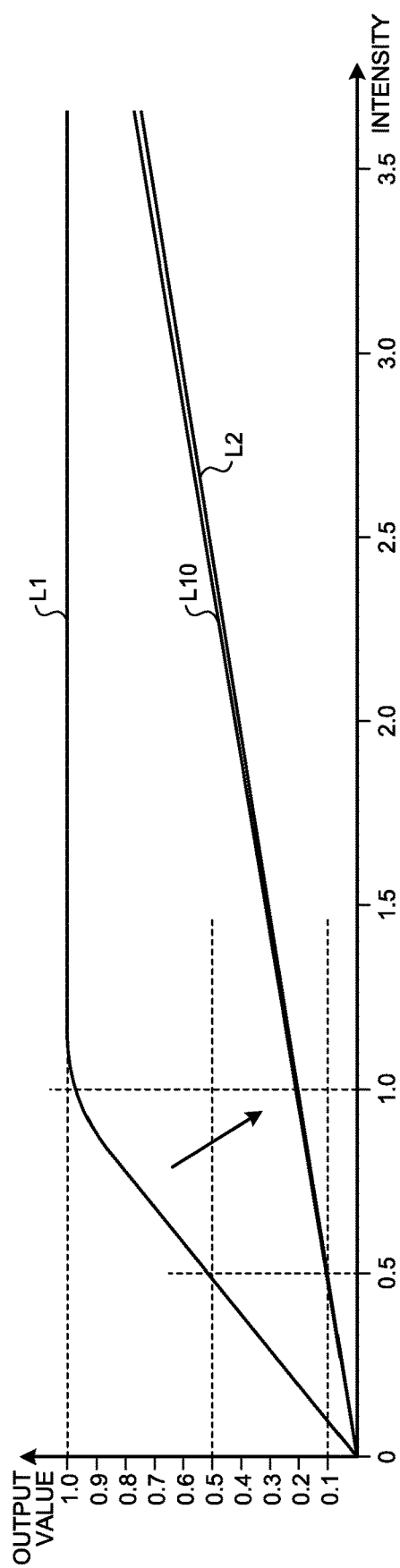
FIG. 9 is a diagram illustrating relations between intensity of special light and output value of each pixel when the light source device according to the first embodiment emits the special light.

Therefore, in this first embodiment, the illumination control unit 84 improves the S/N ratio of each of the R-pixel and the G-pixel by increasing the intensity of the narrow band light emitted by the first light source unit 82a. Further, in this first embodiment, by shortening of the accumulation time, in which the B-pixel is caused to accumulate the optical signal charge, such that the signal value of the B-pixel is not saturated, the timing generating unit 25 enables the output value of each of the R-pixel, G-pixel, and B-pixel to be used as an image signal when the narrow band light is emitted by the light source device 8. Specifically, as illustrated in FIG. 9, by shortening of the accumulation time, in which the B-pixel is caused to accumulate light such that the signal value of the B-pixel is not saturated, the timing generating unit 25 artificially makes spectral characteristics of the B-pixel similar to spectral characteristics of the R-pixel or G-pixel (curve L1→straight line L10), thereby enabling the output value of each of the R-pixel, G-pixel, and B-pixel to be used as an image signal when the narrow band light is emitted by the light source device 8. In this case, the color filter 26 desirably has the above described spectral characteristics in FIG. 4.

Timing of Reading from Each Unit Pixel for White Light

Figure 10:
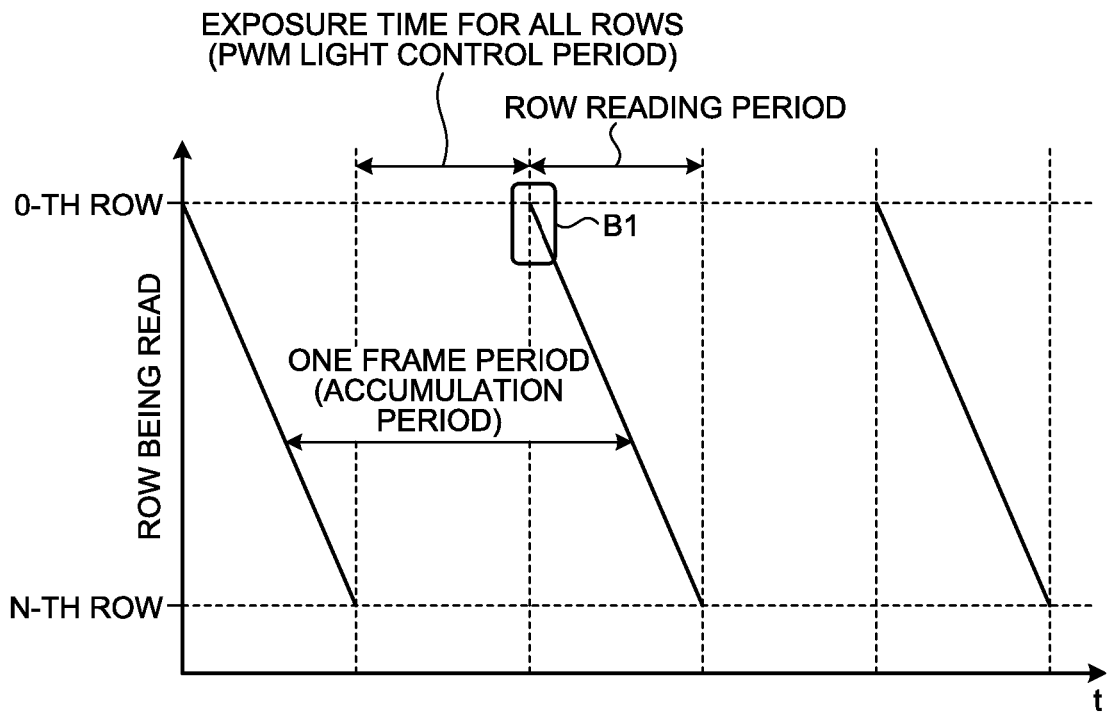
FIG. 10 is a diagram schematically illustrating a timing of reading of a signal from each pixel unit of a light receiving unit by a reading unit, when the light source device according to the first embodiment emits white light.
Figure 11:
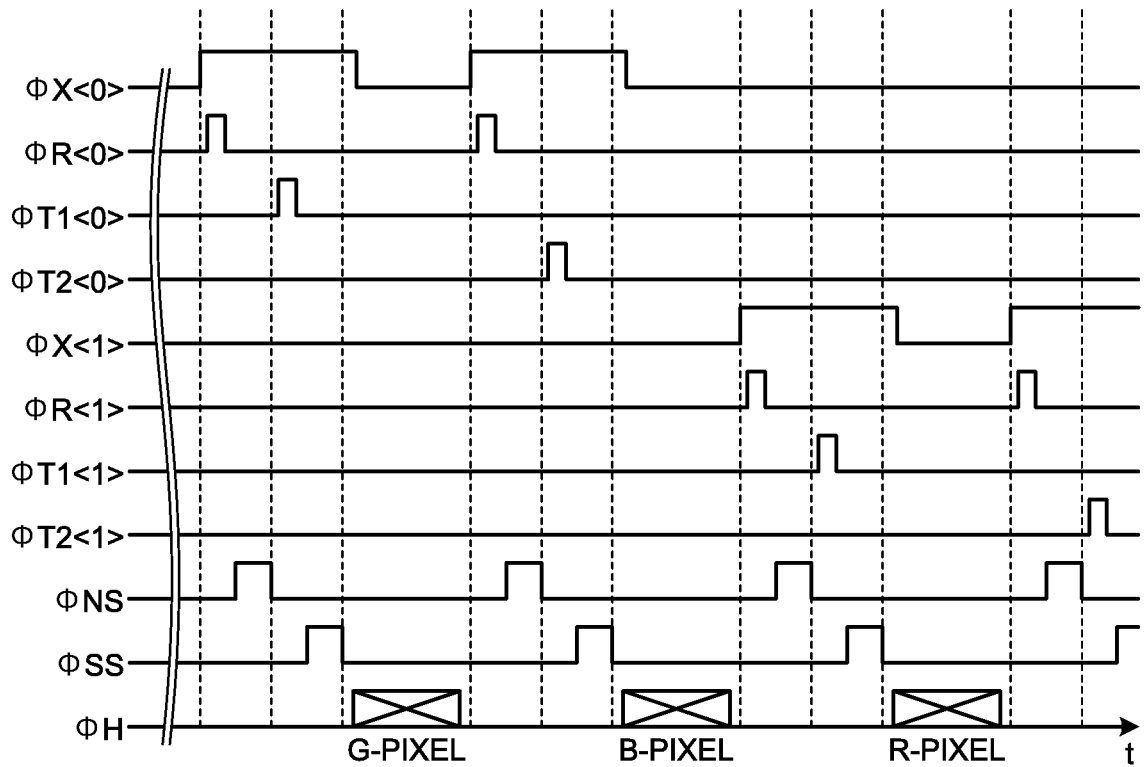
FIG. 11 is a diagram illustrating a timing chart of an enlarged portion of an area B1 in FIG. 10.

Next, a timing of reading from each unit pixel 230 when the light source device 8 emits the white light will be described. FIG. 10 is a diagram schematically illustrating a timing of reading of a signal from each unit pixel 230 of the light receiving unit 23 by the reading unit 24, when the light source device 8 emits the white light. FIG. 11 is a diagram illustrating a timing chart of an enlarged portion of an area B1 in FIG. 10. FIG. 11 is a timing chart for, in order from the top: a row selection pulse ΦX<0>, a drive pulse ΦR<0>, a drive pulse ΦT1<0>, a drive pulse ΦT2<0>, a row selection pulse ΦX<1>, a drive pulse ΦR<1>, a drive pulse ΦT1<1>, a drive pulse ΦT2<1>, the drive pulse ΦNS, the drive pulse ΦSS, and the drive pulse ΦH.

As illustrated in FIG. 10 and FIG. 11, based on each drive pulse input from the timing generating unit 25, the reading unit 24 reads the imaging signal from each unit pixel 230 per horizontal line, and outputs the imaging signal to the buffer 27 of the second chip 22.

As illustrated in FIG. 11, firstly, the timing generating unit 25 turns the row selection pulse ΦX<0> to an ON-state (high).

Subsequently, the timing generating unit 25 turns the drive pulse ΦR<0> to an ON-state (high). Thereby, the charge converter resetting unit 236 resets the charge converter 233 to a predetermined potential.

Thereafter, the timing generating unit 25 turns the drive pulse ΦR<0> to an OFF-state (low), and turns the drive pulse ΦNS to an ON-state (high). Thereby, the first sampling unit 252 is caused to sample a noise signal from the charge converter 233 via the vertical transfer line 239.

Thereafter, the timing generating unit 25 turns the drive pulse ΦT1<0> to an ON-state (high), and turns the drive pulse ΦSS to an ON-state (high). In this case, by the drive pulse ΦT1<0> being supplied to the gate of the transfer transistor 234 from the timing generating unit 25, the transfer transistor 234 is turned to an ON-state, and transfers signal charge from the photoelectric conversion element 231 to the charge converter 233. At this time, the pixel output switch 238 causes the imaging signal voltage-converted by the charge converter 233 to be output from the pixel source follower transistor 237 to the vertical transfer line 239. Further, the second sampling unit 255 samples the imaging signal output from the vertical transfer line 239.

Subsequently, after turning the drive pulse ΦSS to an OFF-state (low), the timing generating unit 25 turns the row selection pulse ΦX<0> to an OFF-state (low) and sequentially repeats the ON/OFF operation for each column of the column selection pulse ΦH<N>. In this case, each second sampling unit 255 transfers the sampled imaging signal of the G-pixel to the second horizontal transfer line 260 for output to the output unit 31. Thereby, the imaging signal of each G-pixel is output.

Thereafter, the timing generating unit 25 turns the row selection pulse ΦX<0> to the ON-state (High).

Subsequently, the timing generating unit 25 turns the drive pulse ΦR<0> to the ON-state (high). In this case, by the drive pulse ΦR<0> being input to the gate of the charge converter resetting unit 236 from the timing generating unit 25, the charge converter resetting unit 236 is turned to an ON-state, and resets the charge converter 233 to a predetermined potential.

Thereafter, the timing generating unit 25 turns the drive pulse ΦR<0> to the OFF-state (low), and turns the drive pulse ΦNS to the ON-state (high). Thereby, the first sampling unit 252 is caused to sample the noise signal from the charge converter 233 via the vertical transfer line 239.

Thereafter, the timing generating unit 25 turns the drive pulse ΦT2<0> to an ON-state (high), and turns the drive pulse ΦSS to the ON-state (high). In this case, by the drive pulse ΦT2<0> being supplied to the gate of the transfer transistor 235 from the timing generating unit 25, the transfer transistor 235 is turned to an ON-state, and transfers the signal charge from the photoelectric conversion element 232 to the charge converter 233. At this time, the pixel output switch 238 causes the imaging signal voltage-converted by the charge converter 233 to be output from the pixel source follower transistor 237 to the vertical transfer line 239. Further, the second sampling unit 255 samples the imaging signal output from the vertical transfer line 239.

Subsequently, after turning the drive pulse ΦSS to the OFF-state (low), the timing generating unit 25 turns the row selection pulse ΦX<0> to the OFF-state (low) and sequentially repeats the ON/OFF operation for each column of the column selection pulse ΦH<N>. In this case, each second sampling unit 255 transfers the sampled imaging signal of the B-pixel to the second horizontal transfer line 260 for output to the output unit 31. Thereby, the imaging signal of each B-pixel is output.

As described above, the reading unit 24 reads an imaging signal from each unit pixel 230 per horizontal line, and outputs the imaging signal to the buffer 27 of the second chip 22.

Timing of Reading from Each Unit Pixel for Narrow Band Light

Figure 12:
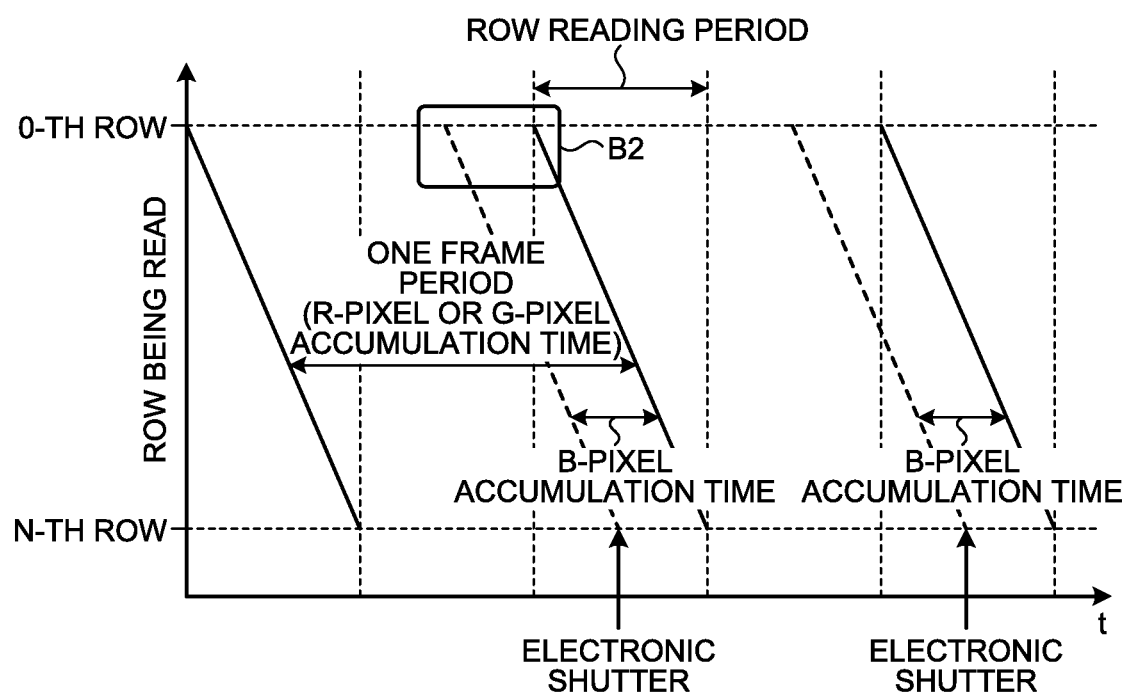
FIG. 12 is a diagram schematically illustrating a timing of reading of a signal from each pixel unit of the light receiving unit by the reading unit, when the light source device according to the first embodiment emits special light.
Figure 13:
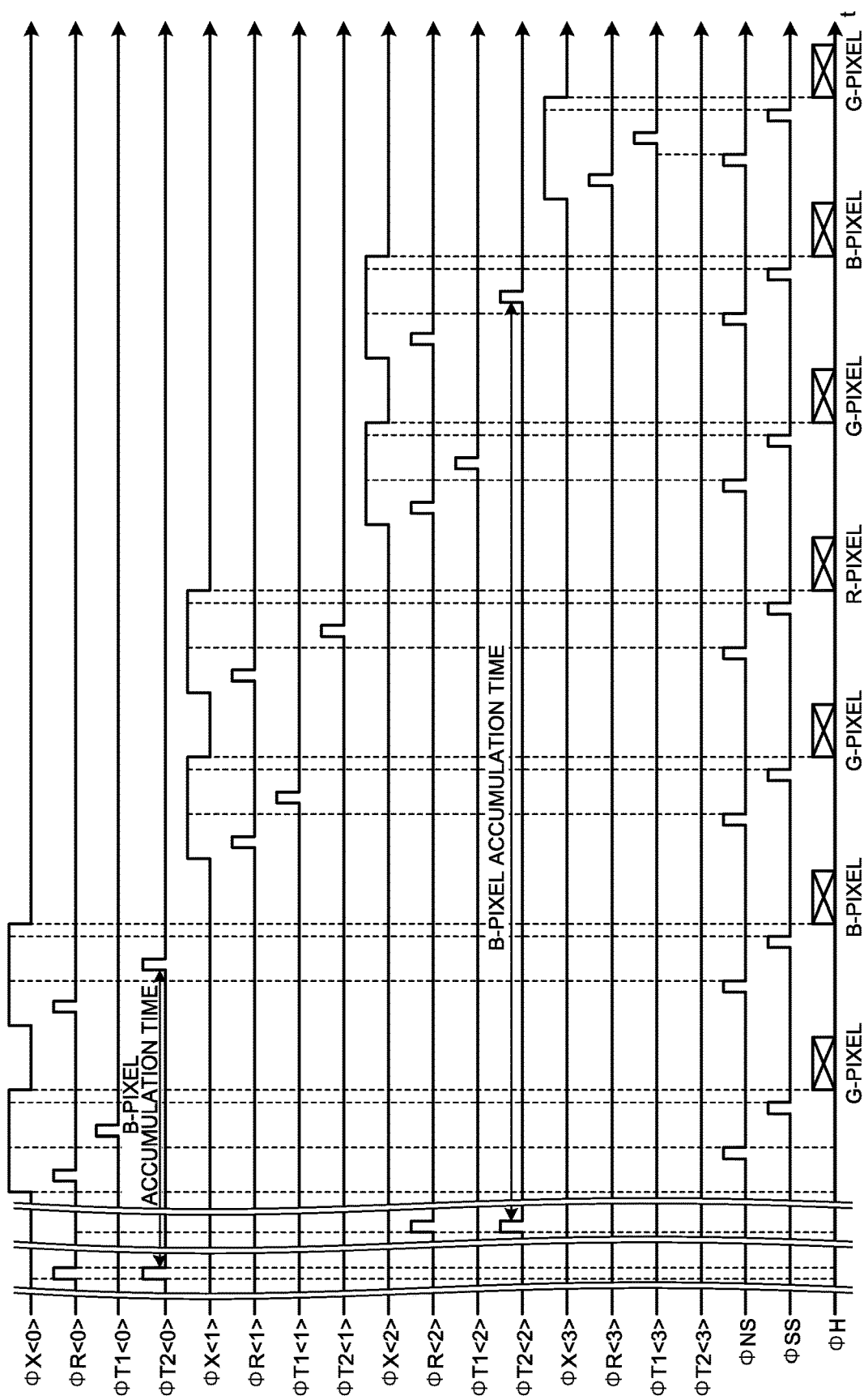
FIG. 13 is a diagram illustrating a timing chart of an enlarged portion of an area B2 in FIG. 12.

Next, a timing of reading from each unit pixel 230 when the light source device 8 emits the narrow band light will be described. FIG. 12 is a diagram schematically illustrating a timing, in which a signal is read from each unit pixel 230 of the light receiving unit 23 by the reading unit 24, when the light source device 8 emits the narrow band light. FIG. 13 is a diagram illustrating a timing chart of an enlarged portion of an area B2 in FIG. 12.

As illustrated in FIG. 12 and FIG. 13, by controlling a timing in which each drive pulse is output, according to sensitivity to the narrow band light (B-light) emitted by the first light source unit 82*a*, the timing generating unit 25 adjusts an accumulation time of each of the G-pixels and R-pixels, and an accumulation time of the B-pixels. Specifically, the timing generating unit 25 controls the accumulation time of the B-pixels with an electronic shutter such that the accumulation time of the B-pixels becomes approximately ⅕ of the accumulation time of each of the G-pixels and R-pixels.

As illustrated in FIG. 13, firstly, the timing generating unit 25 turns each of the drive pulse ΦR<0 and drive pulse ΦT2<0> to the ON-state. Thereby, the signal charge accumulated in the photoelectric conversion element 232 corresponding to the B-pixel is released to the power source voltage VDD. As a result, the signal charge accumulated in the photoelectric conversion element 231 corresponding to the B-pixel is reset. As described above, the timing generating unit 25 controls the accumulation time of the B-pixels with an electronic shutter such that the accumulation time of the B-pixels becomes approximately ⅕ of the accumulation time of each of the G-pixels and R-pixels.

Subsequently, the timing generating unit 25 turns each of the drive pulse ΦR<0> and drive pulse ΦT2<0> to the OFF-state, and executes signal charge accumulation of the B-pixel.

After the accumulation of the signal charge in the B-pixel, the timing generating unit 25 turns the row selection pulse ΦX<0> to the ON-state (high) and turns the drive pulse ΦR to the ON-state (high). Thereby, the charge converter resetting unit 236 is turned to the ON-state, causes the signal charge accumulated in the charge converter 233 to be released, and resets the charge converter 233 to a predetermined potential. Subsequently, the timing generating unit 25 turns the drive pulse ΦNS to the ON-state, and causes the first sampling unit 252 to sample the noise signal input from the charge converter 233 via the vertical transfer line 239.

Subsequently, the timing generating unit 25 turns the drive pulse ΦNS to the OFF-state (low). Thereby, the first sampling unit 252 completes sampling of the noise signal.

Thereafter, the timing generating unit 25 turns the drive pulse ΦT1<0> to the ON-state (high) and turns the drive pulse ΦSS to the ON-state (high). In this case, by the drive pulse ΦT1<0> being supplied to the gate of the transfer transistor 234 from the timing generating unit 25, the transfer transistor 234 is turned to the ON-state, and transfers the signal charge from the photoelectric conversion element 231 to the charge converter 233. At this time, the pixel output switch 238 causes the imaging signal voltage-converted by the charge converter 233 to be output from the pixel source follower transistor 237 to the vertical transfer line 239. Further, the second sampling unit 255 samples the imaging signal output from the vertical transfer line 239.

Subsequently, after turning the drive pulse ΦSS to the OFF-state (low), the timing generating unit 25 turns the row selection pulse ΦX<0> to the OFF-state (low) and sequentially repeats the ON/OFF operation for each column of the column selection pulse ΦH<N>. In this case, each second sampling unit 255 transfers the sampled imaging signal of the G-pixel to the second horizontal transfer line 260 for output to the output unit 31, and each first sampling unit 252 transfers the sampled noise signal to the first horizontal transfer line 259 for output to the output unit 31. The output unit 31 outputs a difference between the imaging signal and the noise signal of each G-pixel, and thereby, the noise-removed imaging signal of each G-pixel is output.

Thereafter, the timing generating unit 25 turns the row selection pulse ΦX<0> to the ON-state (high).

Subsequently, the timing generating unit 25 turns the drive pulse ΦR<0> to the ON-state (high). In this case, by the drive pulse ΦR<0> being input to the gate of the charge converter resetting unit 236 from the timing generating unit 25, the charge converter resetting unit 236 is turned to the ON-state, and resets the charge converter 233 to a predetermined potential.

Thereafter, the timing generating unit 25 turns the drive pulse ΦR<0> to the OFF-state (low), and turns the drive pulse ΦNS to the ON-state (high). In this case, the first sampling switch 251 is turned to an ON-state, and causes the first sampling unit 252 to sample the noise signal input from the charge converter 233 via the vertical transfer line 239.

Subsequently, the timing generating unit 25 turns the drive pulse ΦNS to the OFF-state (low). Thereby, the first sampling unit 252 completes sampling of the noise signal.

Thereafter, the timing generating unit 25 turns the drive pulse ΦT2<0> to the ON-state (high) and turns the drive pulse ΦSS to the ON-state (high). In this case, by the drive pulse ΦT2<0> being supplied to the gate of the transfer transistor 235 from the timing generating unit 25, the transfer transistor 235 is turned to the ON-state, and transfers the signal charge from the photoelectric conversion element 232 to the charge converter 233. At this time, the pixel output switch 238 causes the imaging signal voltage-converted by the charge converter 233 to be output from the pixel source follower transistor 237 to the vertical transfer line 239. Further, the second sampling unit 255 samples the imaging signal output from the vertical transfer line 239.

Subsequently, after turning the drive pulse ΦSS to the OFF-state (low), the timing generating unit 25 turns the row selection pulse ΦX<0> to the OFF-state (low) and sequentially repeats the ON/OFF operation for each column of the column selection pulse ΦH<N>. In this case, each second sampling unit 255 transfers the sampled imaging signal of the B-pixel to the second horizontal transfer line 260 for output to the output unit 31. Thereby, the imaging signal of each B-pixel having the accumulation time that is approximately ⅕ of the accumulation time of each of the G-pixels and R-pixels is output.

As described above, the timing generating unit 25 controls the accumulation time of the B-pixels such that the B-pixels are not saturated, by adjusting the accumulation time of the B-pixels to approximately ⅕ of the accumulation time of each of the G-pixels and R-pixels, by executing the electronic shutter operation.

According to the above described first embodiment, an image having a high resolution is able to be acquired even if irradiation is performed with either of narrow band light and white light, since: the R-filters have the spectral characteristics where the maximum value of their transmission spectrum is in the red wavelength band and the transmittance of the wavelength band of the narrow band light is higher than the transmission spectrum in the green and blue wavelength bands; the G-filters have the spectral characteristics where the maximum value of their transmission spectrum is in the green wavelength band and the transmittance of the wavelength band of the narrow band light is higher than the transmission spectrum in the red and blue wavelength bands; the B-filters have the spectral characteristics where the maximum value of their transmission spectrum is in the blue wavelength band and the transmittance of the wavelength band of the narrow band light is higher than the transmission spectrum in the red and green wavelength bands; and the timing generating unit 25 individually controls the accumulation time, in which each unit pixel 230 is caused to accumulate the optical signal charge.

Further, according to the first embodiment, since the timing generating unit 25 performs control of making the accumulation time of the B-pixels having the highest spectral sensitivity to the narrow band light emitted by the first light source unit 82a shorter than the accumulation time of the unit pixels 230 having the R-filters or the G-filters arranged thereon, for the plural unit pixels 230 each having any one of a red filter, a green filter, and a blue filter arranged thereon; even if the intensity of the narrow band light emitted by the first light source unit 82a is made larger than the intensity of the narrow band light emitted by the second light source unit 82b, the B-pixels are prevented from being saturated.

Further, according to the first embodiment, since the red filters have the spectral characteristics where their transmission spectrum gradually increases toward the short wavelength side from 440 nm, and the green filters have the spectral characteristics where their transmission spectrum gradually increases toward the short wavelength side from 440 nm; even if a subject is irradiated with the white light, color reproducibility is high and color noise is prevented from being generated.

Further, according to the first embodiment, since the illumination control unit 84 controls, based on the sensitivity ratio of each of the R-pixels, G-pixels, and B-pixels, the intensity of the narrow band light emitted by the first light source unit 82a; when the NBI observation mode is used in the endoscope system 1, an image having a high resolution is able to be acquired.

Second Embodiment

Next, a second embodiment will be described. An endoscope system according to this second embodiment has the same configuration as the above described first embodiment, but a timing of reading by a reading unit controlled by a timing generating unit is different from that in the first embodiment. Specifically, the above described timing generating unit 25 according to the first embodiment controls the accumulation times such that the B-pixels are not saturated, by performing the electronic shutter operation in each row, but a timing generating unit according to this second embodiment controls the accumulation times such that the B-pixels are not saturated, by performing shutter operation (global shutter) simultaneously for all rows. Hereinafter, a timing of reading from each pixel unit by the timing generating unit according to this second embodiment will be described. The same reference signs will be appended to configurations that are the same as those of the above described endoscope system 1 according to the first embodiment, and description thereof will be omitted.

Timing of Reading from Each Unit Pixel for Narrow Band Light

Figure 14:
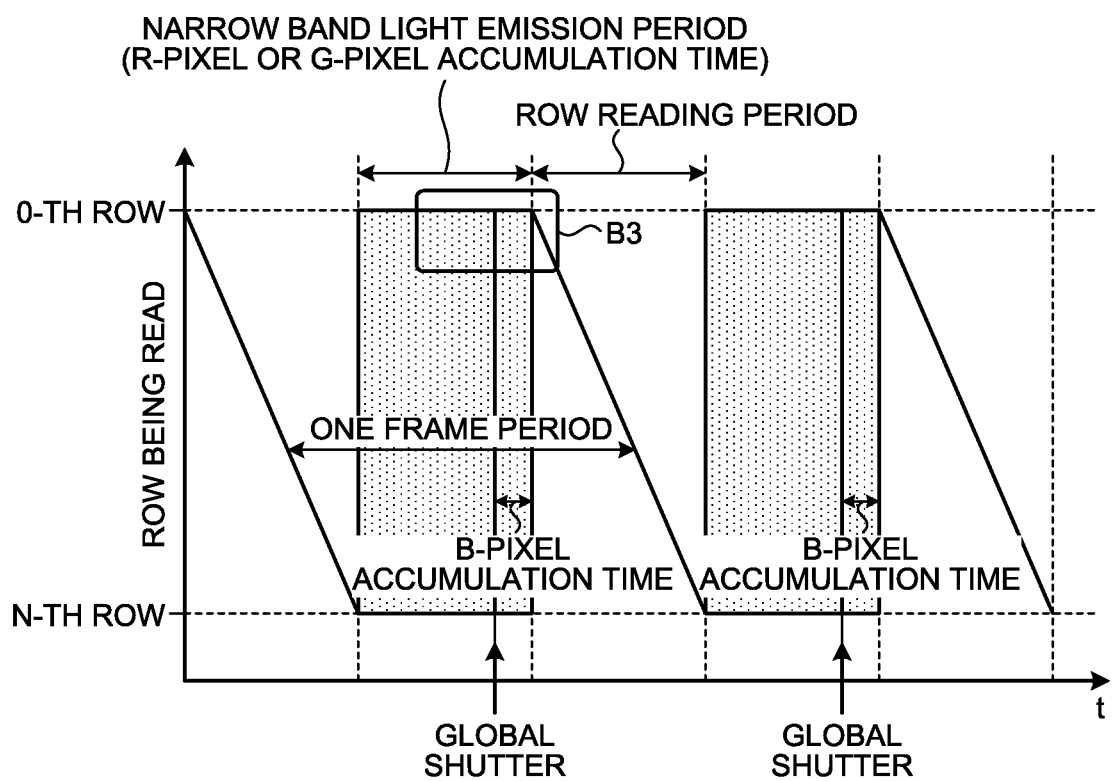
FIG. 14 is a diagram schematically illustrating a timing of reading of a signal from each pixel unit of a light receiving unit by a reading unit, when a light source device according to a second embodiment emits special light.
Figure 15:
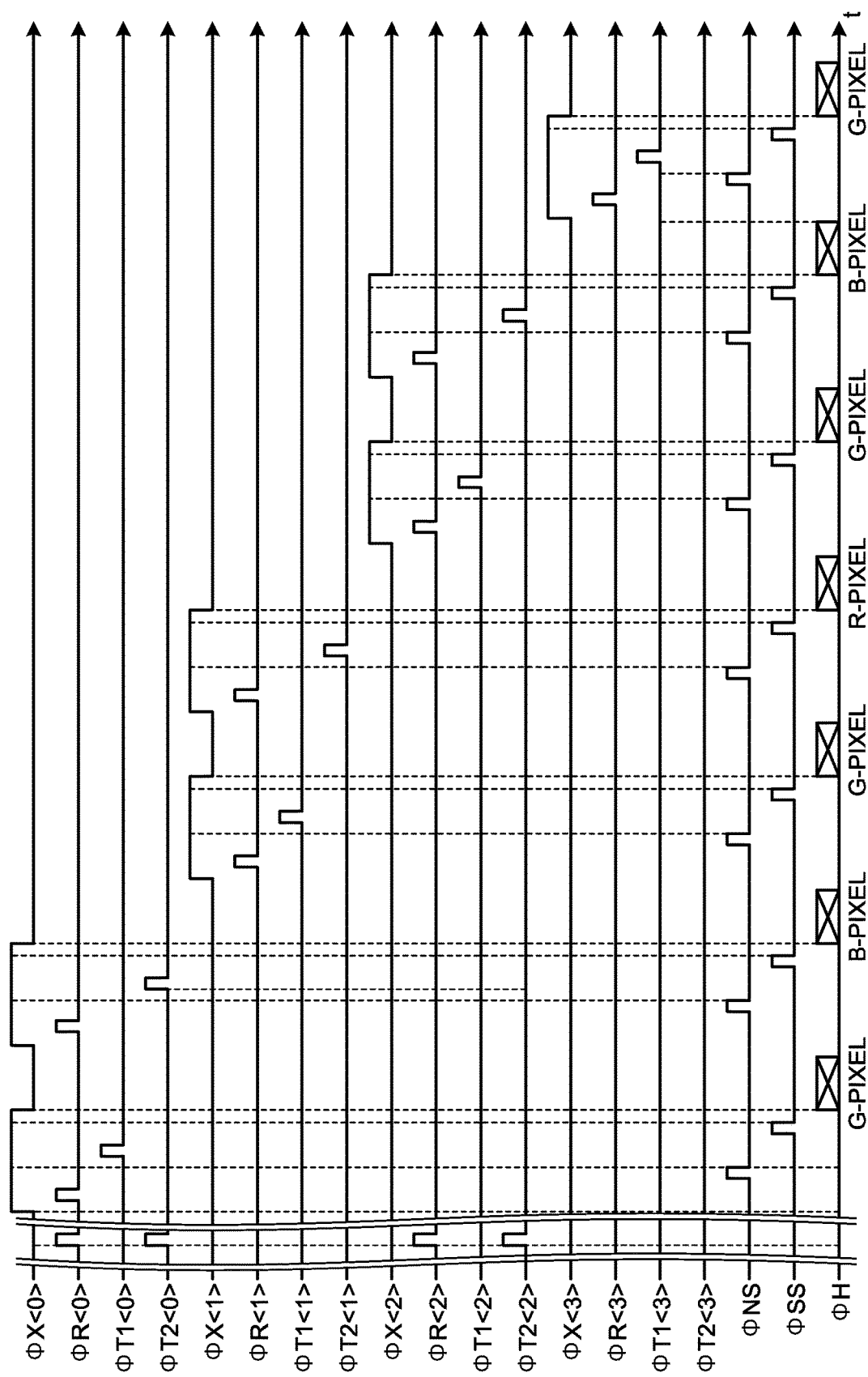
FIG. 15 is a diagram illustrating a timing chart of an enlarged portion of an area B3 in FIG. 14.

FIG. 14 is a diagram schematically illustrating a timing, in which the reading unit 24 reads a signal from each unit pixel 230 of the light receiving unit 23 when the light source device 8 according to the second embodiment emits the narrow band light. FIG. 15 is a diagram illustrating a timing chart for an enlarged portion of an area B3 in FIG. 14.

As illustrated in FIG. 14, by controlling a timing in which each drive pulse is output, according to sensitivity to the narrow band light (B-light) emitted by the first light source unit 82a, the timing generating unit 25 adjusts an accumulation time of each of the G-pixels and R-pixels, and an accumulation time of the B-pixels. Specifically, the timing generating unit 25 controls the accumulation time of the B-pixels with a global shutter such that the accumulation time of the B-pixels becomes approximately ⅕ of the accumulation time of each of the G-pixels and R-pixels. Further, by executing PWM control, the illumination control unit 84 performs irradiation with narrow band light in a period (narrow band light emission period) other than a reading period, in which the reading unit 24 reads imaging signals from the light receiving unit 23.

As illustrated in FIG. 15, firstly, the timing generating unit 25 simultaneously turns each of drive pulses ΦR<0, 2, 4, . . . , m> of even-numbered lines and drive pulses ΦT2<0, 2, 4, . . . , m-2, m> of the even-numbered lines to an ON-state. Thereby, the signal charge accumulated in the photoelectric conversion elements 232 corresponding to the B-pixels is released to the power source voltage VDD. As a result, the signal charge accumulated in the photoelectric conversion elements 231 corresponding to the B-pixels is reset. As described above, the timing generating unit 25 controls the accumulation time of the B-pixels with a global shutter (electronic shutter) such that the accumulation time of the B-pixels becomes approximately ⅕ of the accumulation time of each of the G-pixels and R-pixels.

Subsequently, the timing generating unit 25 turns each of the drive pulses ΦR<0, 2, 4, . . . , m> and drive pulses ΦT2<0, 2, 4, . . . , m> to the OFF-state, and executes signal charge accumulation of the B-pixels.

After accumulating the signal charge of the B-pixels, the timing generating unit 25 turns the row selection pulse ΦX<0> to the ON-state (high) and turns the drive pulse ΦR to the ON-state (high). Thereby, the charge converter resetting unit 236 is turned to the ON-state, causes the signal charge accumulated in the charge converter 233 to be released, and resets the charge converter 233 to a predetermined potential. Subsequently, the timing generating unit 25 turns the drive pulse ΦNS to the ON-state, and causes the first sampling unit 252 to sample the noise signal input from the charge converter 233 via the vertical transfer line 239.

Subsequently, the timing generating unit 25 turns the drive pulse ΦNS to the OFF-state (low). Thereby, the first sampling unit 252 completes sampling of the noise signal.

Thereafter, the timing generating unit 25 turns the drive pulse ΦT1<0> to the ON-state (high) and turns the drive pulse ΦSS to the ON-state (high). In this case, by the drive pulse ΦT1<0> being supplied to the gate of the transfer transistor 234 from the timing generating unit 25, the transfer transistor 234 is turned to the ON-state, and transfers the signal charge from the photoelectric conversion element 231 to the charge converter 233. At this time, the pixel output switch 238 causes the imaging signal voltage-converted by the charge converter 233 to be output from the pixel source follower transistor 237 to the vertical transfer line 239. Further, the second sampling unit 255 samples the imaging signal output from the vertical transfer line 239.

Subsequently, after turning the drive pulse ΦSS to the OFF-state (low), the timing generating unit 25 turns the row selection pulse ΦX<0> to the OFF-state (low) and sequentially repeats the ON/OFF operation for each column of the column selection pulse ΦH<N>. In this case, each second sampling unit 255 transfers the sampled imaging signal of the G-pixel to the second horizontal transfer line 260 for output to the output unit 31, and each first sampling unit 252 transfers the sampled noise signal to the first horizontal transfer line 259 for output to the output unit 31. The output unit 31 outputs a difference between the imaging signal and the noise signal of each G-pixel, and thereby, the noise-removed imaging signal of each G-pixel is output.

Thereafter, the timing generating unit 25 turns the row selection pulse ΦX<0> to the ON-state (high).

Subsequently, the timing generating unit 25 turns the drive pulse ΦR<0> to the ON-state (high). In this case, by the drive pulse ΦR<0> being input to the gate of the charge converter resetting unit 236 from the timing generating unit 25, the charge converter resetting unit 236 is turned to the ON-state, and resets the charge converter 233 to a predetermined potential.

Thereafter, the timing generating unit 25 turns the drive pulse ΦR<0> to the OFF-state (low), and turns the drive pulse ΦNS to the ON-state (high). In this case, the charge converter resetting unit 236 is turned to the ON-state, causes the signal charge accumulated in the charge converter 233 to be released, and resets the charge converter 233 to a predetermined potential. Further, the first sampling switch 251 is turned to the ON-state, and causes the first sampling unit 252 to sample the noise signal input from the charge converter 233 via the vertical transfer line 239.

Subsequently, the timing generating unit 25 turns the drive pulse ΦNS to the OFF-state (low). Thereby, sampling of the noise signal is completed.

Thereafter, the timing generating unit 25 turns the drive pulse ΦT2<0> to the ON-state (high) and turns the drive pulse ΦSS to the ON-state (high). In this case, by the drive pulse ΦT2<0> being supplied to the gate of the transfer transistor 235 from the timing generating unit 25, the transfer transistor 235 is turned to the ON-state, and transfers the signal charge from the photoelectric conversion element 232 to the charge converter 233. At this time, the pixel output switch 238 causes the imaging signal voltage-converted by the charge converter 233 to be output from the pixel source follower transistor 237 to the vertical transfer line 239. Further, the second sampling unit 255 samples the imaging signal output from the vertical transfer line 239.

Subsequently, after turning the drive pulse ΦSS to the OFF-state (low), the timing generating unit 25 turns the row selection pulse ΦX<0> to the OFF-state (low) and sequentially repeats the ON/OFF operation for each column of the column selection pulse ΦH<N>. In this case, each second sampling unit 255 transfers the sampled imaging signal of the B-pixel to the second horizontal transfer line 260 for output to the output unit 31. Thereby, the imaging signal of each B-pixel having the accumulation time that is approximately ⅕ of the accumulation time of each of the G-pixels and R-pixels is output.

As described above, the timing generating unit 25 controls the accumulation time (exposure time) of the B-pixels such that the B-pixels are not saturated, by adjusting the accumulation time, in which the B-pixels are caused to accumulate the optical signal charge, to be approximately ⅕ of the accumulation time of each of the G-pixels and R-pixels, by executing the global shutter operation.

The above described second embodiment has effects that are similar to the above described effects of the first embodiment, and, even if irradiation is performed with either of narrow band light and white light, an image having a high resolution is able to be acquired.

Further, according to the second embodiment, since the timing generating unit 25 executes, by using the global shutter, control of making the accumulation time of the B-pixels shorter than the accumulation time of each of the R-pixels and G-pixels, image distortion (rolling shutter phenomenon) is able to be prevented infallibly.

Third Embodiment

Next, a third embodiment will be described. An endoscope system according to this third embodiment has a configuration different from that of the above described first embodiment, and controls accumulation times according to sensitivity ratios of the filters respectively provided on the pixels. Hereinafter, after description of a configuration of the endoscope system according to the third embodiment, a timing of reading from each pixel unit of the endoscope system according to the third embodiment will be described. The same reference signs will be appended to configurations that are the same as those of the above described endoscope system 1 according to the first embodiment, and description thereof will be omitted.

Configuration of Endoscope System

Figure 16:
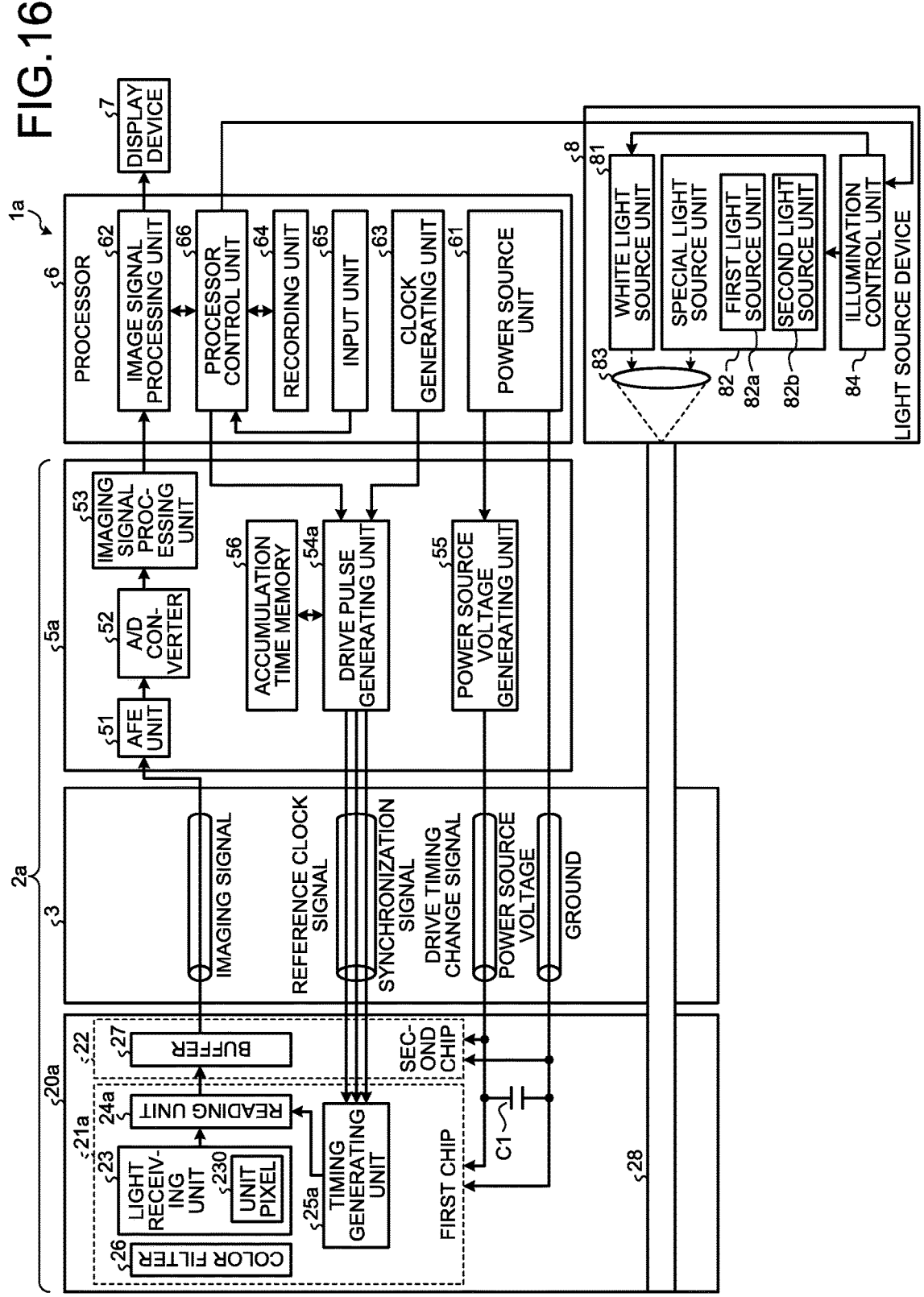
FIG. 16 is a block diagram illustrating functions of main parts of an endoscope system according to a third embodiment.

FIG. 16 is a block diagram illustrating functions of main parts of the endoscope system according to the third embodiment. An endoscope system 1a illustrated in FIG. 16 includes an endoscope 2a, instead of the endoscope 2 of the above described endoscope system 1 according to the first embodiment. The endoscope 2a includes an imaging unit 20a, the transmission cable 3, and a connector unit 5a.

The connector unit 5a has the AFE unit 51, the A/D converter 52, the imaging signal processing unit 53, a drive pulse generating unit 54a, the power source voltage generating unit 55, and an accumulation time memory 56.

Based on a reference clock signal supplied from the processor 6 and serving as reference of operation of each unit forming the endoscope 2a, the drive pulse generating unit 54a generates a synchronization signal indicating a start position of each frame, and outputs the synchronization signal, together with the reference clock signal, to the timing generating unit 25 of the imaging unit 20, via the transmission cable 3. Further, based on type information (power source information) indicating a type of the power source of the light source device 8, the type information being input from the processor 6, the drive pulse generating unit 54a outputs a drive timing change signal for instructing change of a drive timing to a first chip 21a (imaging element) in the imaging unit 20a, to the timing generating unit 25 of the first chip 21a. The synchronization signal generated by the drive pulse generating unit 54 includes a horizontal synchronization signal and a vertical synchronization signal.

The accumulation time memory 56 records therein an accumulation time for each of the R-filters, G-filters, and B-filters in the color filter 26 arranged on the light receiving surface of each of the plural unit pixels 230, for each light source, the accumulation time corresponding to a sensitivity ratio (transmittance). For example, as listed in a table T1 illustrated in FIG. 17 and indicating a sensitivity ratio of each filter for each light source, sensitivities of an R-filter and a G-filter to the special light source are lower than a sensitivity of a B-filter, and sensitivities of the R-filter and the G-filter to the white light source are substantially the same. Therefore, ratios among amounts of light transmitted through the respective color filters arranged on the unit pixels 230 differ between the special light source and the white light source, and thus if accumulation times are made the same for all of the unit pixels 230, their signal charge numbers (=sensitivities) differ depending on the filters. Since saturation charge numbers of the unit pixels 230 are limited, their signal charge numbers are desirably about the same. Therefore, as illustrated in FIG. 18, the accumulation time memory 56 records therein a table T2 indicating accumulation time information related to accumulation times set according to reciprocals of the sensitivity ratios of the respective filters for each of the light sources. Thereby, by the accumulation times according to the sensitivity ratios of the respective filters being recorded for each of the light sources, output at an appropriate signal level is enabled without any of the pixels being saturated.

The imaging unit 20a has the first chip 21a and the second chip 22. The first chip 21a has the light receiving unit 23, a reading unit 24a, the timing generating unit 25, and the color filter 26. A detailed configuration of the first chip 21a will be described later.

Figure 19:
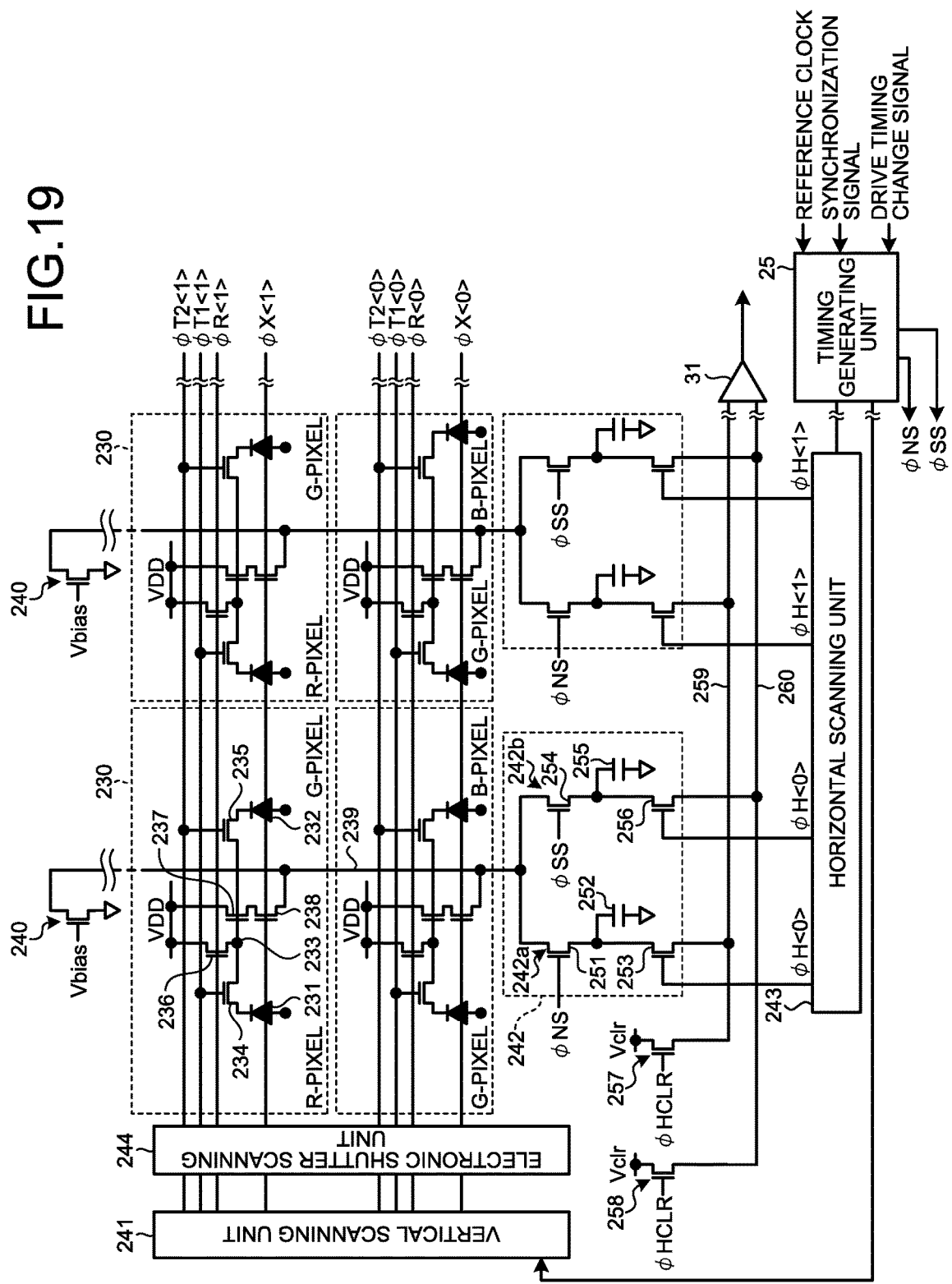
FIG. 19 is a circuit diagram illustrating a detailed configuration of a first chip illustrated in FIG. 16.

Next, the detailed configuration of the first chip 21a mentioned above will be described. FIG. 19 is a circuit diagram illustrating a configuration of the first chip 21a.

The first chip 21a illustrated in FIG. 19 includes at least: the timing generating unit 25; the output unit 31 (amplifier); the plural pixels 230; the constant current source 240; the vertical scanning unit 241 (row selecting circuit); the CDS unit 242; the horizontal scanning unit 243 (column selecting circuit); an electronic shutter scanning unit 244; the first horizontal resetting transistor 257; and the second horizontal resetting transistor 258. The vertical scanning unit 241, the horizontal scanning unit 243, and the electronic shutter scanning unit 244 function as the reading unit 24.

Based on the reference clock signal, the synchronization signal, and the drive timing change signal, a timing generating unit 25a generates various drive pulses, and outputs the various drive pulses respectively to the vertical scanning unit 241, the electronic shutter scanning unit 244, the CDS unit 242, and the horizontal scanning unit 243. In this third embodiment, the timing generating unit 25a functions as a control unit that controls, according to a sensitivity of each filter, an accumulation time, in which each of the plural unit pixels 230 is caused to accumulate optical signal charge.

Based on drive pulses (for example, ΦX, ΦR, ΦT1, and ΦT2) input from the timing generating unit 25, the vertical scanning unit 241 and the electronic shutter scanning unit 244 drive unit pixels 230 of rows different from each other. The electronic shutter scanning unit 244 selectively applies ΦR, and ΦT1<M> or ΦT2<M>, respectively to unit pixels 230 having color filters installed thereon, for which saturation is desired to be prevented by shortening of accumulation times of the unit pixels 230, and causes the unit pixels 230 to discharge signal charge (imaging signals) to the power source voltage VDD. By selecting plural rows simultaneously, the electronic shutter scanning unit 244 is able to arbitrarily set accumulation times for the unit pixels 230 corresponding to all of the color filters.

In the first chip 21a configured as described above, based on the drive pulses (for example, ΦX, ΦR, ΦT1, and ΦT2) input from the timing generating unit 25, the vertical scanning unit 241 and the electronic shutter scanning unit 244 drive unit pixels 230 of rows different from each other, and the electronic shutter scanning unit 244 causes unit pixels 230, which are installed with color filters, for which saturation is desired to be prevented by shortening of accumulation times of the unit pixels 230, to discharge signal charge (imaging signals) to the power source voltage VDD, by selectively applying ΦR, and ΦT1<M> or ΦT2<M> respectively to these unit pixels 230. Thereby, by selection of unit pixels 230 having the same color filters arranged thereon from the unit pixels 230 of the rows selected by the electronic shutter scanning unit 244 and application of the same pixel resetting signal (ΦR) as that for the vertical scanning unit 241, accumulation times of optical signal charge accumulated in the unit pixels 230 are controlled.

The above described third embodiment has effects that are similar to the above described effects of the first embodiment, and, even if irradiation is performed with either of narrow band light and white light, an image having a high resolution is able to be acquired.

Further, according to the third embodiment, by the timing generating unit 25 controlling the electronic shutter scanning unit 244 and the vertical scanning unit 241, accumulation times of unit pixels 230 are controlled according to accumulation times corresponding to sensitivity ratios of their filters for each light source, and thus output at an appropriate signal level is enabled without any of the unit pixels 230 being saturated.

Other Embodiments

Further, according to the above described embodiments, the timing generating unit controls only the accumulation times, in which the B-pixels accumulate the optical signal charge, but for example, a timing generating unit may make accumulation times, in which the R-pixels are caused to accumulate the optical signal charge for narrow band light shorter than accumulation times, in which the G-pixels are caused to accumulate the optical signal charge. For example, based on a ratio between sensitivities of the R-pixels and the G-pixels to the narrow band light, the timing generating unit may make the accumulation times of the R-pixels shorter than the accumulation times of the G-pixels. Of course, based on the respective sensitivities of the B-pixels, R-pixels, and G-pixels to the narrow band light, the timing generating unit may make accumulation times of the B-pixels shorter than the accumulation times of the R-pixels, and make accumulation times of the R-pixels shorter than the accumulation times of the B-pixels (accumulation times of B-pixels<accumulation times of R-pixels<accumulation times of G-pixels).

Further, according to the above described embodiments, the special light source unit emits the narrow band light included in the blue wavelength band, but a special light source unit may emit narrow band light included in, for example, an infrared or near-infrared wavelength band.

Further, according to the above described embodiments, the color filter in a Bayer array using the R-filters, G-filters, and B-filters is used, but a color filter formed of, for example, complementary color filters including cyan, magenta, and yellow filters may be used.

Further, the above described embodiments are applied to an endoscope inserted in a subject, but the embodiments are also applicable to, for example, a capsule type endoscope, or an imaging device that captures an image of a subject.

In the description of the flow charts in this specification, the context of the processing among the steps is disclosed by use of expressions such as "firstly", "thereafter", and "subsequently"; but sequences of the processing necessary for implementation are not uniquely defined by these expressions. That is, the sequences of the processing in the flow charts described in this specification may be modified as far as no contradiction arises from the modification.

Accordingly, the present disclosure may include various embodiments not described herein, and various design changes and the like within the scope of the technical ideas specified by the scope of the claims may be made.

The present disclosure has an effect of enabling an image having a high resolution to be acquired, even if irradiation is performed with either of narrow band light and white light.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging device for capturing an image of a subject irradiated with white light including a red wavelength band, a green wavelength band, and a blue wavelength band, or with narrow band light of a narrow band narrower than a wavelength band of the white light, and generating image data, the imaging device comprising:
  plural pixels arranged in a two-dimensional matrix, and configured to receive light from outside, generate imaging signals according to amounts of the received light, and output the imaging signal via one of vertical lines, the plural pixels having a horizontal two-shared pixel configuration for outputting the imaging signal by sharing one vertical line between horizontally neighboring two pixels;
  a color filter comprising:
    a blue filter having spectral characteristics where a maximum value of its transmission spectrum is in the blue wavelength band and transmittance of the wavelength band of a narrow band light is higher than the transmission spectrum in the red and green wavelength bands;
    a red filter having spectral characteristics where a maximum value of its transmission spectrum is in the red wavelength band and a minimum value of its transmission spectrum is near the maximum value of the transmission spectrum of the blue wavelength band, and having spectral characteristics where its transmission spectrum gradually increases toward a short wavelength side from 440 nm; and
    a green filter having spectral characteristics where a maximum value of its transmission spectrum is in the green wavelength band and a minimum value of its transmission spectrum is near the maximum value of the transmission spectrum of the blue wavelength band, and having spectral characteristics where its transmission spectrum gradually increases toward a short wavelength side from 440 nm,
    wherein the blue filter, the red filter, and the green filter are respectively arranged correspondingly to the plural pixels; and
  a controller configured to execute control of making an accumulation time of a pixel of the plural pixels shorter than accumulation times of pixels having other filters arranged thereon, the pixel having highest spectral sensitivity to the narrow band light.

2. The imaging device according to claim 1,
  wherein the controller is configured to, when the imaging device captures an image of the subject irradiated with the narrow band light, individually control the accumulation times of the plural pixels respectively, based on spectral sensitivity ratios of the plural pixels.

3. The imaging device according to claim 1,
  wherein the plural pixels share one vertical line between horizontally neighboring two pixels to output the imaging signal.

4. The imaging device according to claim 3,
  wherein the narrow band is 390 nm to 440 nm, and
  wherein the controller is configured to execute control of making an accumulation time of a pixel having the blue filter arranged thereon shorter than accumulation times of pixels having the red filter and the green filter arranged thereon.

5. The imaging device according to claim 4,
  wherein the red filter and the green filter have spectral characteristics where their transmission spectra gradually increase toward a short wavelength side from 440 nm.

6. The imaging device according to claim 4,
  wherein the controller is configured to control the accumulation time of the pixel having the blue filter arranged thereon by electronic shutter operation.

7. The imaging device according to claim 6, further comprising:
  a transfer gate configured to transfer the imaging signal from each of the plural pixels,
  wherein the controller is configured to execute the electronic shutter operation by outputting a shutter pulse to a transfer gate of the pixel having the blue filter arranged thereon, in an accumulation period, in which the pixel having the blue filter thereon receives light.

8. The imaging device according to claim 2, further comprising:
  a vertical scanning circuit configured to select a row of the plural pixels; and
  an electronic shutter scanning circuit configured to select a row of the plural pixels and cause the imaging signal therein to be discharged,
  wherein the controller is configured to individually control the accumulation times of the plural pixels, by causing the same pixel resetting signal as that for the vertical scanning circuit to be output to the electronic shutter scanning circuit, after causing the vertical scanning circuit and the electronic shutter scanning circuit to select the rows that are different from each other, and causing the electronic shutter scanning circuit to select, from pixels of the row selected by the electronic shutter scanning circuit, pixels having filters of the same color arranged thereon.

9. The imaging device according to claim 1,
  wherein the controller is configured to execute, for every line in a horizontal direction, control of making an accumulation time of a pixel of the plural pixels having the horizontal two-shared pixel configuration shorter than accumulation times of pixels having other filters arranged thereon, the pixel having highest spectral sensitivity to the narrow band light.

10. An endoscope, comprising:
  an insertion portion configured to be insertable in the subject; and
  the imaging device according to claim 1, at a distal end of the insertion portion.

11. The endoscope according to claim 10, further comprising:
  a connector configured to be connected to a processor that executes image processing on image data corresponding to the imaging signal; and
  a memory provided in the connector and configured to record therein accumulation time information indicating the accumulation time of each of the plural pixels having any one of the red filter, green filter, and blue filter arranged thereon for the white light or narrow band light,
  wherein the controller is configured to individually control the accumulation times of the plural pixels respectively, based on the accumulation time information recorded in the memory.

12. The endoscope according to claim 11,
  wherein the controller is configured to individually control the accumulation times of the plural pixels respectively, based on type information indicating a type of illumination light and the accumulation time information that are input from the processor.

13. An endoscope system, comprising:
the endoscope according to claim 10;
a light source configured to emit the narrow band light; and
an illumination controller configured to control intensity of the narrow band light and causes the light source to emit the narrow band light, based on a sensitivity ratio of each of the plural pixels having any one of the blue filter, the red filter and the green filter arranged thereon.

* * * * *